US011110594B2

United States Patent
Oguri et al.

(10) Patent No.: US 11,110,594 B2
(45) Date of Patent: Sep. 7, 2021

(54) FINE WORK ASSISTANCE SYSTEM AND FINE WORK MANIPULATOR

(71) Applicant: Kyushu University, National University Corp., Fukuoka (JP)

(72) Inventors: Susumu Oguri, Fukuoka (JP); Makoto Hashizume, Fukuoka (JP); Masaharu Murata, Fukuoka (JP)

(73) Assignee: Kyushu University, National University Corp., Fukuoka (JP)

( * ) Notice: Subject to any disclaimer, the term of this patent is extended or adjusted under 35 U.S.C. 154(b) by 727 days.

(21) Appl. No.: 15/773,858

(22) PCT Filed: Nov. 1, 2016

(86) PCT No.: PCT/JP2016/082468
§ 371 (c)(1),
(2) Date: May 4, 2018

(87) PCT Pub. No.: WO2017/078022
PCT Pub. Date: May 11, 2017

(65) Prior Publication Data
US 2019/0160650 A1 May 30, 2019

(30) Foreign Application Priority Data

Nov. 5, 2015 (JP) .............................. JP2015-217912

(51) Int. Cl.
*A61B 34/37* (2016.01)
*B25J 7/00* (2006.01)
(Continued)

(52) U.S. Cl.
CPC ................ *B25J 7/00* (2013.01); *A61B 34/30* (2016.02); *A61B 34/37* (2016.02); *A61B 34/72* (2016.02);
(Continued)

(58) Field of Classification Search
CPC ..... A61B 19/201; A61B 19/203; A61B 19/52; A61B 19/44; A61B 19/20; A61B 19/22;
(Continued)

(56) References Cited

U.S. PATENT DOCUMENTS 6,786,896 B1 * 9/2004 Madhani ................ B25J 9/1615
606/1
2003/0233102 A1 * 12/2003 Nakamura ......... A61B 17/3476
606/130

FOREIGN PATENT DOCUMENTS

JP 2003079638 A 3/2003
JP 2010514512 A 5/2010
(Continued)

OTHER PUBLICATIONS

Takumi Harada, Koji Ikuta, "Development of the Water Pressure Drive Remote Surgical Robot" Robotics Society of Japan, Sep. 17, 2012, RSJ2012AC2L2-5, particularly, 1. to 3.
(Continued)

*Primary Examiner* — Vi X Nguyen
(74) *Attorney, Agent, or Firm* — Duquette Law Group, LLC

(57) ABSTRACT

A fine work assistance system is configured such that a parallel link mechanism is used for a slave manipulator activated by a master operation, and a precise motion for microsurgery or the like is performed by remote control. In a slave unit of a master-slave manipulator, the parallel link mechanism with multiple degrees of freedom is used for a link mechanism in which an end effector is movable with respect to a base. Moreover, a tip operation part is driving by a hydraulic driving mechanism such that a plurality of linear actuators supported by the base move one ends of links so as to move the end effector, and the slave unit is activated in response to a user operation on the master unit. This (Continued)

achieves the precise motion of the end effector and causes the end effector to perform operations for a precise work.

8 Claims, 18 Drawing Sheets

(51) Int. Cl.
| | | |
|---|---|---|
| *A61B 90/00* | (2016.01) | |
| *B25J 9/00* | (2006.01) | |
| *A61B 34/00* | (2016.01) | |
| *B25J 9/12* | (2006.01) | |
| *B25J 3/04* | (2006.01) | |
| *B25J 19/00* | (2006.01) | |
| *B25J 9/14* | (2006.01) | |
| *B25J 15/02* | (2006.01) | |
| *B25J 13/02* | (2006.01) | |
| *B25J 15/04* | (2006.01) | |
| *B25J 3/00* | (2006.01) | |
| *A61B 34/30* | (2016.01) | |

(52) U.S. Cl.
CPC .............. *A61B 34/74* (2016.02); *A61B 34/76* (2016.02); *A61B 90/03* (2016.02); *A61B 90/37* (2016.02); *B25J 3/00* (2013.01); *B25J 3/04* (2013.01); *B25J 9/0042* (2013.01); *B25J 9/123* (2013.01); *B25J 9/144* (2013.01); *B25J 13/025* (2013.01); *B25J 15/022* (2013.01); *B25J 15/04* (2013.01); *B25J 19/0083* (2013.01); *A61B 2034/304* (2016.02); *A61B 2090/064* (2016.02)

(58) Field of Classification Search
CPC . A61B 19/2203; A61B 19/50; A61B 19/5244; A61B 17/3403; A61B 34/30; A61B 34/37; A61B 34/72; A61B 34/74; B25J 3/00

See application file for complete search history.

(56) References Cited

FOREIGN PATENT DOCUMENTS

| | | |
|---|---|---|
| JP | 2010260139 A | 11/2010 |
| JP | 2015100677 A | 6/2015 |
| JP | 2015525095 A | 9/2015 |
| WO | 9910137 A1 | 3/1999 |

OTHER PUBLICATIONS

International Search Report dated Apr. 4, 2017 From Corresponding International Application No. PCT/JP2016/082468.

* cited by examiner

US 11,110,594 B2

FINE WORK ASSISTANCE SYSTEM AND FINE WORK MANIPULATOR

This patent application is a U.S. National Application Filed Under 35 U.S.C. 371 of International Application No. PCT/JP2016/082468, filed on Nov. 1, 2016 which claims the benefit of Japanese Patent Application No. 2015-217912, filed on Nov. 5, 2015.

TECHNICAL FIELD

The present invention relates to a fine work assistance system that assists a work by handling a minute object under remote control, and particularly relates to a fine work assistance system that can make precise motion for microsurgery, precise handling of living organisms such as small animals, and handling of minute units such as cells.

BACKGROUND ART

In so-called microsurgery, for example, surgery is performed relative to minute surgery objects under a microscope such as anastomosises of thin blood vessels having a diameter of about 0.5 to 2 mm, nerves, and lymph vessels in orthopedic surgery, plastic surgery, and reconstruction of defects. In such surgery, highly accurate and precise works and expertise are required because of minute objects. Moreover, such surgery is so difficult as to be performed over an extended time, increasing a burden on a surgeon. For this reason, microsurgery can be performed by only a limited number of surgeons with a low frequency, though the surgery has grown in demand.

Thus, the use of manipulators (robots) that have greatly advanced with regard to technology in recent years has been examined. A master-slave manipulator can perform scaled-down human motions as well as duplicated human motions. If motions for surgery are performed by a precisely operating manipulator, a burden on a surgeon can be reduced and the efficiency of surgery is expected to increase while eliminating the influence of shaky hands or the like so as to ensure accuracy.

In surgery other than microsurgery, for example, endoscopic surgery, telesurgery has been already practically used with manipulators. This has successfully reduced a burden on a surgeon because a manipulator can increase workability with a larger range of motion than a human surgeon and allows the surgeon to always operate the manipulator in a comfortable position with an ensured field of view.

For example, JP 2015-525095 A discloses an endoscopic surgical system according to the related art, in which a surgical motion can be remotely performed using a master-slave manipulator.

CITATION LIST

Patent Literature

Patent Literature 1: JP 2015-525095 A

SUMMARY OF INVENTION

Technical Problem

The surgical system according to the related art is configured as shown in the patent literature. In a slave-side manipulator that performs a surgical motion, a serial link mechanism that can increase a movable range (work area) is used as a movable mechanism for obtaining multiple degrees of freedom in terms of the characteristics of endoscopic surgery.

It seems that the manipulator for endoscopic surgery according to the related art is easily applied to microsurgery. In microsurgery requiring precise works, however, a surgical operation is seriously affected by defects unique to the serial link mechanism, e.g., the accumulation of link movement errors. Thus, it has been quite difficult to apply the related-art manipulator to microsurgery.

Against this backdrop, manipulators that can make precise motions for microsurgery have not become commercially practical. In the field of microsurgery, a surgical system including a manipulator is not usable as a substitute for a surgeon who performs surgery. Thus, a burden on the surgeon cannot be reduced.

An object of the present invention, which has been made to solve the problem, is to provide a fine work assistance system, in which a parallel link mechanism with multiple degrees of freedom is used for a slave manipulator activated in response to an operation of a master, so that a precise motion can be made for fine work of microsurgery or the like and the motions of the work are properly made by a remote operation and efficiently assist the work so as to reduce a burden on an operator, and a fine work manipulator used for the fine work assistance system.

Solution to Problem

A fine work assistance system according to the present invention includes a master-slave manipulator, in which a slave unit performs a predetermined operation for fine work on a work object in response to input of a user operation to a master unit of the manipulator, the fine work assistance system including: an imaging unit that captures an image of the work object; and a display unit that enlarges the work object image captured by the imaging unit and displays the image for visual check by a user, the slave unit having a parallel link mechanism with at least 3 degrees of freedom, the parallel link mechanism including a base that is supported in a predetermined location in a space where the work object is present, an end effector that handles the work object or a work instrument, and a plurality of links that are disposed in parallel between the base and the end effector, the parallel link mechanism being capable of changing a position and orientation of the end effector in a predetermined range relative to the base, wherein the parallel link mechanism includes a plurality of linear actuators, each linearly moving one end of the link and moving the end effector connected to the other end of the link, the end effector includes a tip operation part that handles the work object or the work instrument with at least 1 degree of freedom in addition to a motion of the overall parallel link mechanism different from that of the end effector, and a hydraulic driving mechanism that produces a motion for handling the work object or the work instrument by the tip operation part, the master unit includes an operation input unit that receives a user operation, and a support mechanism unit that is capable of acquiring information on a position and orientation of the operation input unit while movably supporting the operation input unit with the same degree of freedom as the parallel link mechanism, the operation input unit has an input mechanism that changes a fluid pressure of hydraulic fluid in response to a predetermined user operation independent of an operation for moving the overall operation input unit, the input mechanism being connected to the hydraulic driving mechanism in the end effector of the slave unit so as to pass the hydraulic fluid through a pipe, and the hydraulic driving mechanism activates the tip operation part in response to a change of a fluid pressure of hydraulic fluid by a user operation on the input mechanism in the operation input unit.

In the present invention, the parallel link mechanism with multiple degrees of freedom is used as the link mechanism in which the end effector is movable relative to the fixed base in the slave unit of the master-slave manipulator. Moreover, the end effector is operated by moving one ends of the links by means of the linear actuators supported by the base, the linear actuators of the slave unit are activated and the position and orientation of the end effector are changed in response to a user operation for changing the position and orientation of the operation input unit of the master unit. Thus, a precise motion can be achieved for the end effector in the simple and rigid link mechanism where errors are hardly accumulated. Also in a remote operation by a user who is viewing a captured image on the display, operations for fine work, for example, microsurgery can be performed by the end effector. The same motions can be reproduced as the techniques of skilled workers and workability can be improved to reduce the burden of the user.

In the end effector, the tip operation part for actually handling a fine work object or a work instrument is activated by hydraulic driving, a user operation for the input mechanism in the operation input unit is transmitted as a change of fluid pressure to the end effector, and then the tip operation part is operated. Thus, through hydraulic fluid flowing between the operation input unit and the end effector, the tip operation part can be operated by a driving force substantially proportionate to the operating force of the user, a reaction force applied to the tip operation part can be fed back to the input mechanism through a hydraulic transmission system, and the user can handle a fine work object or a work instrument without applying an excessive force to the work object or the work instrument through the tip operation part while properly feeling the tip operation part in contact with any object from the sense of operation of the input mechanism, thereby achieving high operability and safe fine work. The tip operation part is hydraulically driven and thus does not need to be provided with a sensor for detecting a force unlike in motor driving. This can eliminate the need for a complicated work, e.g., calibration of a sensor, reduce the size of the end effector, and easily sterilize the end effector in, for example, use for surgery.

In the fine work assistance system according to the present invention, the linear actuator of the slave unit is optionally a moving-coil linear motor configured such that a coil constitutes a part of a mover and a permanent magnet constitutes a part of a stator, the mover includes a linear-motion slider that is disposed so as to linearly move relative to the base, and the coil that is shaped like a cylinder integrally attached to the linear-motion slider, the coil being disposed with an axial direction parallel to the moving direction of the slider, and the stator includes a cylindrical permanent magnet shorter than the coil, the permanent magnet being fixed to the base so as to be aligned with the coil in a cylinder axial direction, the coil movably penetrating the cylinder inner space of the permanent magnet.

In the present invention, the linear actuators of the slave unit are linear motors, the coils of the linear motors constitute a part of the mover and are disposed so as to linearly move with the linear-motion slider, and the permanent magnet is fixed as a part of the stator with the coil penetrating into the permanent magnet. Thus, the actuator is the linear motor with a small number of components and mechanically movable parts. As a friction resistance is suppressed by reducing contact parts where sliding or rolling appears, high response is achieved when the actuators including the linear motors are activated to move one ends of the links and operate the end effector. This suppresses power consumption for driving. Moreover, the permanent magnet, which generates magnetic fields with a greater impact on surroundings than the coil, is disposed as the stator in a minimum arrangement, whereas the coil is operated as the mover that generates magnetic fields with a relatively small impact on the surroundings. Thus, when the linear motors are activated to move the links, magnetic interference between the linear motors can be prevented to suppress malfunctions of the linear motors, thereby more accurately operating the linear motors with the end effector disposed in a desired position and orientation.

In the fine work assistance system according to the present invention, the linear motors serving as the linear actuators are optionally disposed in parallel in the moving direction of the mover, the coil of the mover is disposed on the base around a predetermined virtual center line extending in parallel with the moving direction of the mover such that the coil is closest to the virtual center line, each of the linear motors includes a magnetic shield member which has a predetermined cross-sectional shape and is disposed around the coil and over the movable range of the coil, and at least the coil is shielded from other coils by the magnetic shield member.

In the present invention, the linear motors constituting the linear actuators of the slave unit are arranged around the predetermined virtual center line with the movers moving in parallel with one another. Moreover, the coils of the movers are disposed near the center of the linear motors. Thus, the coils of the movers in the linear motors are collectively disposed near the virtual center line; meanwhile, the linear-motion sliders integrated with the coils are disposed outside the linear motors, achieving an entirely compact structure. This allows the provision of the multiple slave units near the work object so as to efficiently conduct a fine work in cooperation among the slave units, and the compact structure ensures a work space for operators around the slave units. Cooperation between the slave units and the operators is expected to improve the safety and reliability of fine works. Furthermore, since the magnetic shield members are disposed around the coils of the linear motors, even if the coils of the linear motors are close to each other, magnetic fields generated on the coils upon activation of the linear motors can be reliably prevented from affecting other linear motors. Thus, the slave units can be downsized and the end effector can be correctly operated by activating the linear motors with high precision.

In the fine work assistance system according to the present invention, the parallel link mechanism of the slave unit is optionally a mechanism with at least 6 degrees of freedom in which the linear actuators and the at least six links are disposed in parallel.

In the present invention, the parallel link mechanism of the slave unit is a link mechanism with at least 6 degrees of freedom. Thus, substantially the same operation as a manual operation can be reproduced by the end effector and operations for fine works can be properly performed by the end effector, achieving efficient fine works.

In the fine work assistance system according to the present invention, the end effector of the slave unit optionally has a predetermined range part including the tip operation part such that at least the predetermined range part is replaceable with another separately from joint parts connected to the other ends of the links in the parallel link mechanism.

In the present invention, the predetermined range part can be replaced with another except for the joint parts connected to the links in the end effector of the slave unit. The predetermined range part are optionally replaced with another so as to provide the end effector with another function. An operation can be performed according to the situation by replacing the predetermined range part of the end effector with another at least one time during a work according to the process and purpose of the work. This can improve efficiency in a series of fine works.

The fine work assistance system according to the present invention optionally further includes a sheet-type cover provided over the slave unit except for the predetermined range part replaceable with another separately from the joint parts of the end effector, and the predetermined range part of the end effector is detachably attached to the joint parts even if the cover is provided.

In the present invention, the cover is provided over a part other than the predetermined range part of the end effector actually close to the work object in the slave unit, and the cover isolates the area of parts other than the slave unit from the predetermined range part of the end effector and the area of the work object. Thus, in the application to, for example, surgery, a cover for blocking bacteria or the like is provided over the parts other than the slave unit so as to securely prevent the passage of bacteria or the like from the parts where the presence of a movable mechanism prevents sterilization and cleanliness is hardly obtained. Moreover, in the predetermined range part of the end effector that can be sterilized with a relatively simple structure, the movable mechanism of parts other than the slave unit is not affected and treatment such as sterilization can be securely performed on a part for actually handling a surgery object and a surgical instrument. This can secure cleanliness in the area of the surgery object.

In the fine work assistance system according to the present invention, the input mechanism of the operation input unit optionally has a hydraulic cylinder mechanism in which the volume of a hydraulic fluid room in a cylinder changes according to a movement of an internal piston reciprocating in response to a user operation, and the hydraulic cylinder mechanism includes a rolling diaphragm that divides the interior of the cylinder into the area of the internal piston and the hydraulic fluid room while being deformed according to the movement of the internal piston, the rolling diaphragm keeping a fluid-tight state between the internal piston and the hydraulic fluid room.

In the present invention, the hydraulic cylinder mechanism including the rolling diaphragm is provided as the input mechanism of the operation input unit, the rolling diaphragm keeps a fluid-tight state between the internal piston and the hydraulic fluid room in the cylinder while being deformed according to the movement of the internal piston of the hydraulic cylinder mechanism in response to a user operation, and a pressure is transmitted between the internal piston and hydraulic fluid without causing a loss. A friction resistance for moving the internal piston is suppressed while keeping a fluid-tight state in the cylinder, the operation of the input mechanism smoothly moves the internal piston so as to change a fluid pressure, and the user can easily operate the input mechanism with a small force, thereby improving operability.

In the fine work assistance system according to the present invention, the support mechanism unit of the master unit optionally includes a braking unit capable of generating a braking force as a reaction force against an operating force for moving the operation input unit by the user, and when the end effector of the slave unit moved in response to the user operation on the operation input unit reaches a movable limit position, the braking unit is activated to apply a predetermined braking force in response to a user operation for further moving the operation input unit of the master unit to an area outside the movable limit of the slave unit.

In the present invention, the support mechanism unit of the master unit includes the braking unit that generates a braking force against an operating force for moving the operation input unit. When the end effector of the slave unit reaches the movable limit position, in an operation for further moving the operation input unit of the master unit to an area outside the movable limit of the end effector, the braking unit is activated to apply a braking force as a resistance to an operating force for moving the operation input unit. The braking notifies the user who operates the operation input unit of a resistance force. This can reliably inform the user of the master unit that the end effector has reached the movable limit and cannot move any more, thereby preventing an excessive movement of the operation input unit. This allows the user to efficiently operate the operation input unit and increase the efficiency of fine works conducted through the operation input unit.

A fine work manipulator according to the present invention is a fine work manipulator that performs a predetermined operation for a fine work on a work object in place of a human operator, the manipulator having a parallel link mechanism with at least 3 degrees of freedom, the parallel link mechanism including: a base that is supported in a predetermined location in a space where the work object is present; an end effector that handles the work object or a work instrument; and a plurality of links disposed in parallel between the base and the end effector, wherein a position and orientation of the end effector are variable with respect to the base in a predetermined range, the parallel link mechanism causes a plurality of linear actuators supported by the base to linearly move one ends of the respective links and move the end effector connected to the other ends of the links, the end effector includes a tip operation part that handles the work object or the work instrument with at least 1 degree of freedom in addition to a motion of the overall parallel link mechanism, and a hydraulic driving mechanism that produces a motion for handling the work object or the work instrument with the tip operation part, and the hydraulic driving mechanism receives a change of fluid pressure of hydraulic fluid from the outside and produces a motion for handling the work object or the work instrument with the tip operation part.

In the present invention, the parallel link mechanism with multiple degrees of freedom is used as a link mechanism where the end effector is movable relative to the base on the fixed side in the manipulator, the end effector is operated by moving one ends of the links with the linear actuators supported by the base. According to a predetermined instruction setting of the position and orientation of the end effector, the linear actuators are activated to change the position and orientation of the end effector. Thus, a precise motion can be achieved for the end effector in the simple and rigid link mechanism where errors are hardly accumulated, so that the end effector can perform fine and precise operations required for fine works.

DESCRIPTION OF EMBODIMENTS

Figure 1:
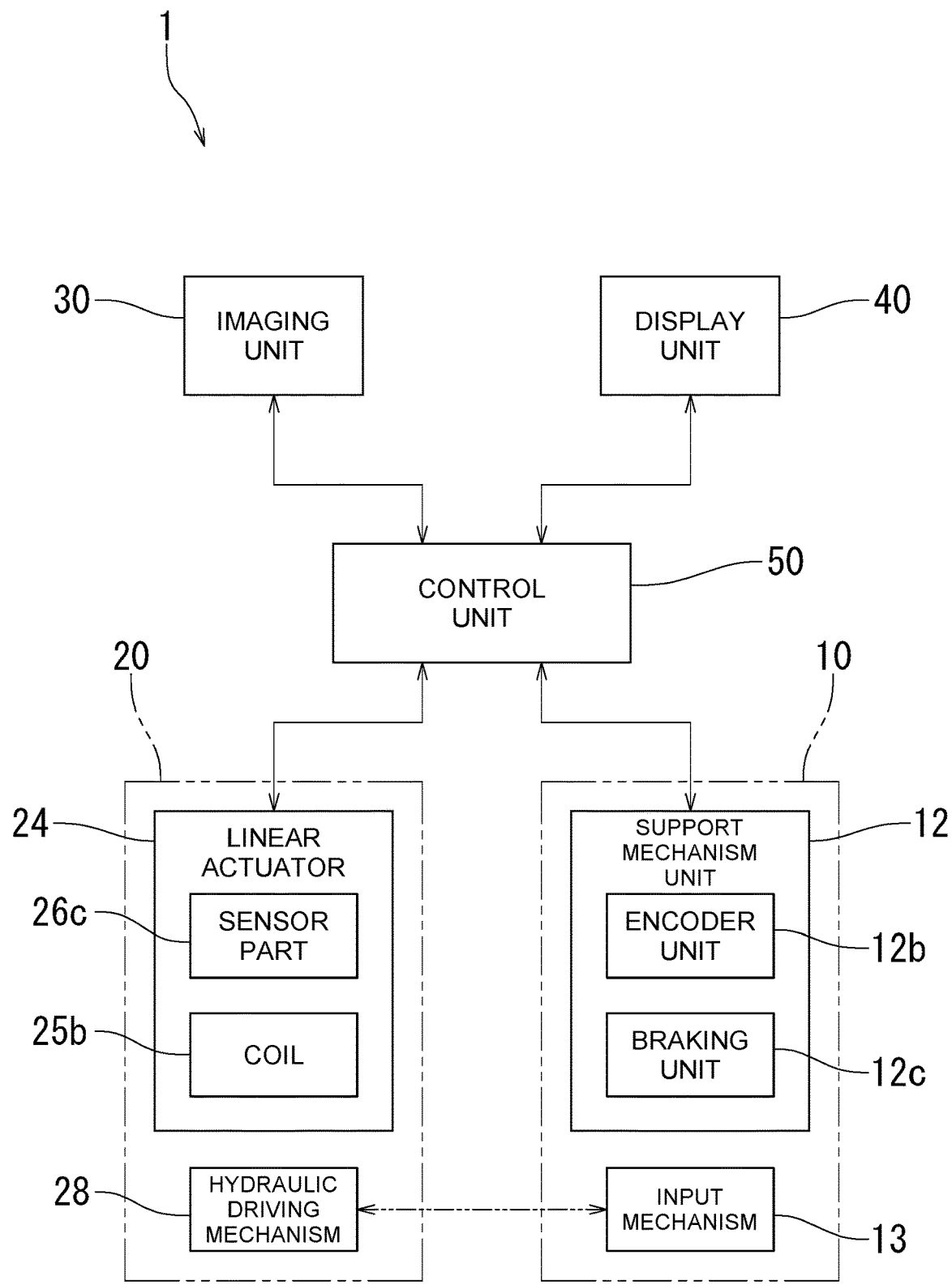
FIG. 1 is a block diagram showing a fine work assistance system according to an embodiment of the present invention.
Figure 2:
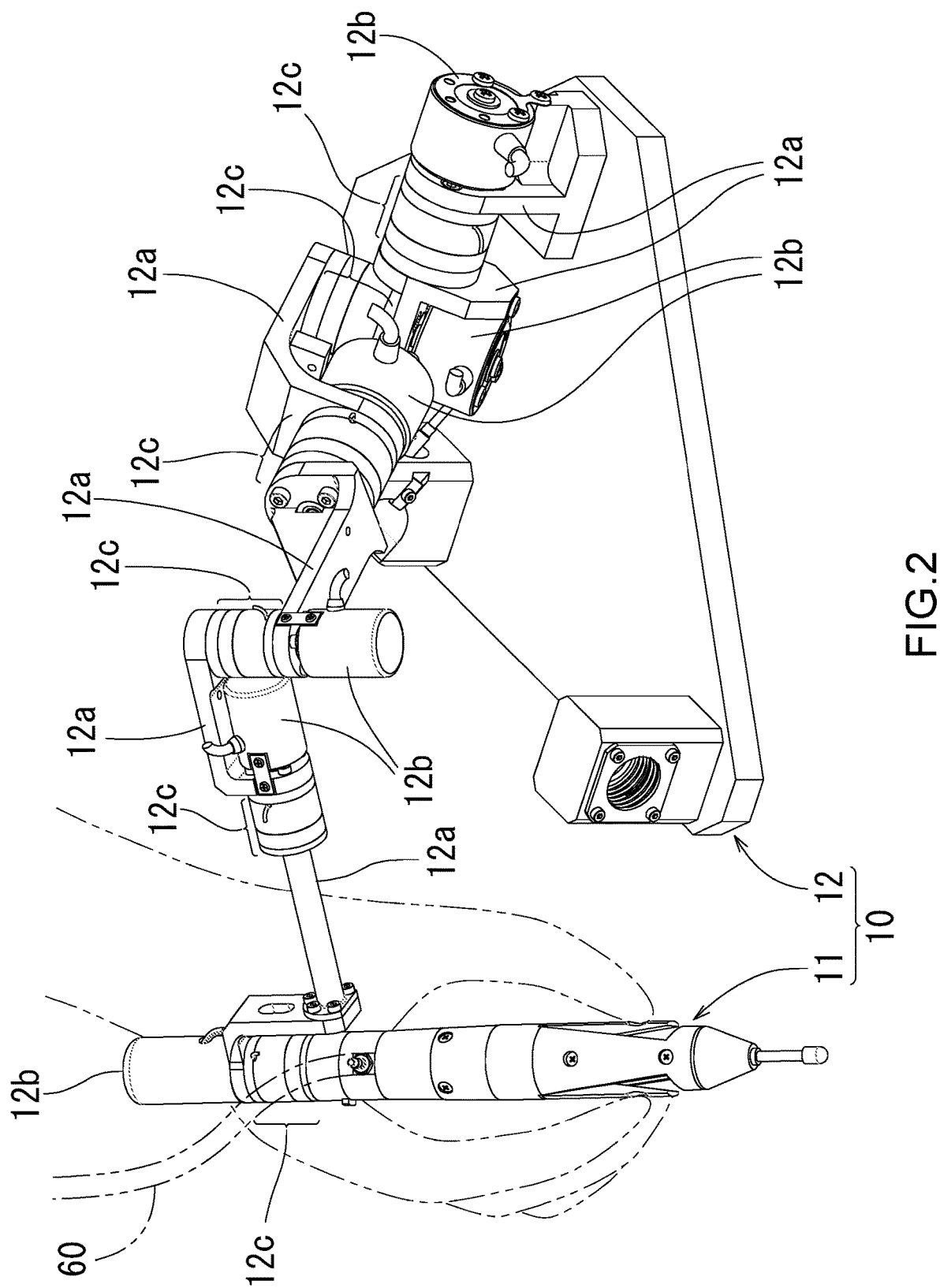
FIG. 2 is a schematic perspective view showing a master unit in the fine work assistance system according to the embodiment of the present invention.

Referring to FIGS. 1 to 20, a fine work assistance system according to an embodiment of the present invention will be described below. The present embodiment will be described as an example of a surgery assistance system for microsurgery performed as a fine work.

In the drawings, a fine work assistance system 1 according to the present embodiment includes a master unit 10 and a slave unit 20 that act as a master-slave manipulator, an imaging unit 30 that captures an image of a surgery object, a display unit 40 that displays the enlarged surgery object image which is captured by the imaging unit 30 and is viewable by a user, and a control unit 50 that controls the movement of the slave unit 20 in response to the master unit 10 moved by the user.

The master unit 10 includes an operation input unit 11 that receives a user operation, and a support mechanism unit 12 that can acquire information on the position and orientation of the operation input unit 11 while movably supporting the operation input unit 11.

The operation input unit 11 has a substantially rod body that can be held with fingers. The operation input unit 11 is connected to one end of the support mechanism unit 12 and is supported with a variable position and orientation (see FIG. 2). The operation input unit 11 includes an input mechanism 13 that changes the fluid pressure of hydraulic fluid in response to a predetermined operation for moving a part of the operation input unit 11 by user. The predetermined operation is independent of an operation for moving the overall operation input unit 11.

The operation input unit 11 may include input means (e.g., a switch) other than the input mechanism 13. In the operation for moving the overall operation input unit 11, for example, instructions may be provided for the following operations: the operations of the imaging unit and the display unit, changing of the ratio of the movement of the slave unit relative to the movement of the master unit, switching of a point of view relative to a surgery object, switching of the slave unit to be operated, starting and terminating of use of an energy device acting as a tip-end actuating part, and discharging of wash water from an end effector.

The input mechanism 13 is attached so as to be partially exposed at two points opposed to each other on the outer surface of the operation input unit 11. The input mechanism 13 includes a pair of lever parts 13a, each being swung by a user operation pressing into the operation input unit with a pinch by two fingers of the user, a hydraulic cylinder part 13b that is contained in the operation input unit 11 and changes the fluid pressure of the hydraulic fluid (e.g., water or oil) according to the movement of a rod 13c and a piston 13d that operate in synchronization with the motion of the lever parts 13a, and a spring 13e that is contained in the operation input unit 11 so as to be compressed according to the movement of the rod 13c when the user presses the lever parts 13a. If the user releases the lever parts 13a, the spring 13e can be urged so as to move the rod 13c with an elastic restoring force and return the lever parts 13a to the original position.

Figure 3:
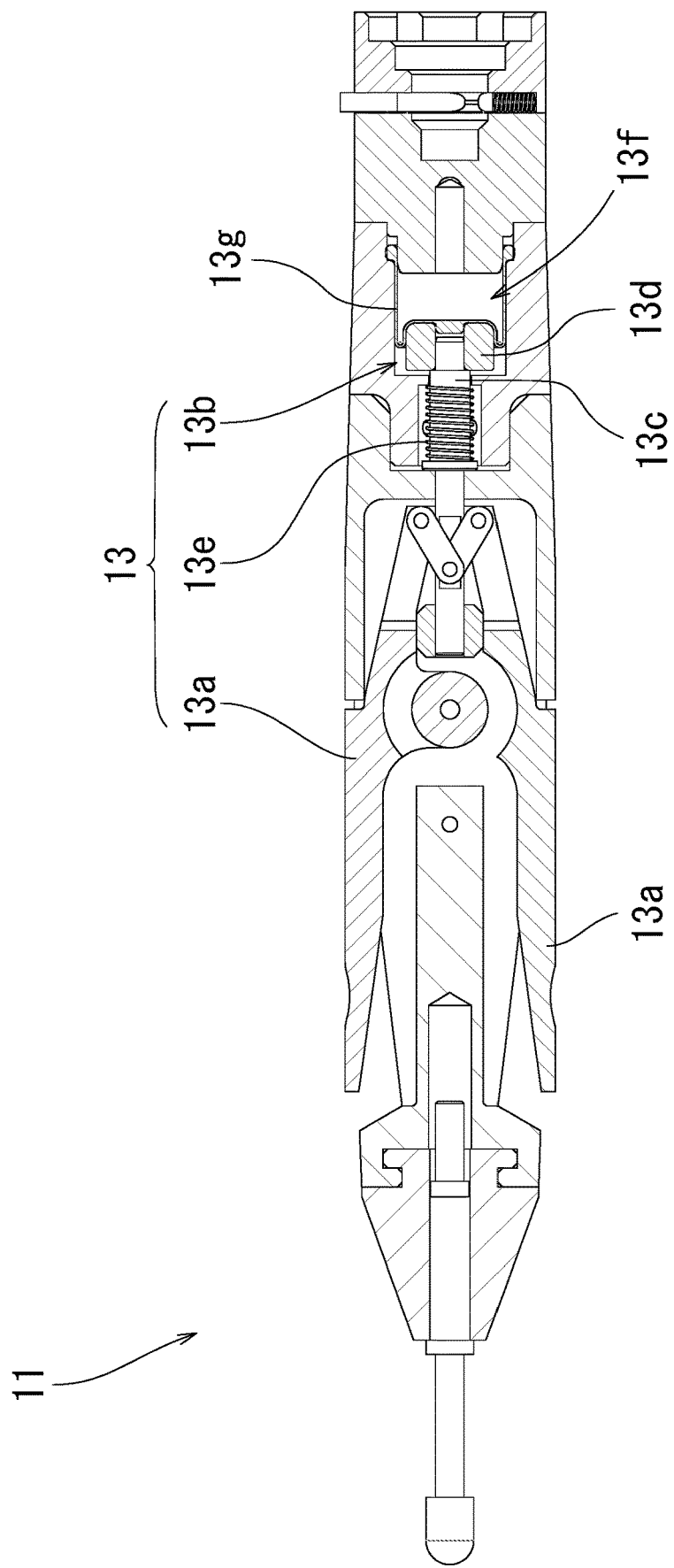
FIG. 3 is an explanatory drawing showing an opening state of lever parts for an operation input unit in the master unit of the fine work assistance system according to the embodiment of the present invention.
Figure 4:
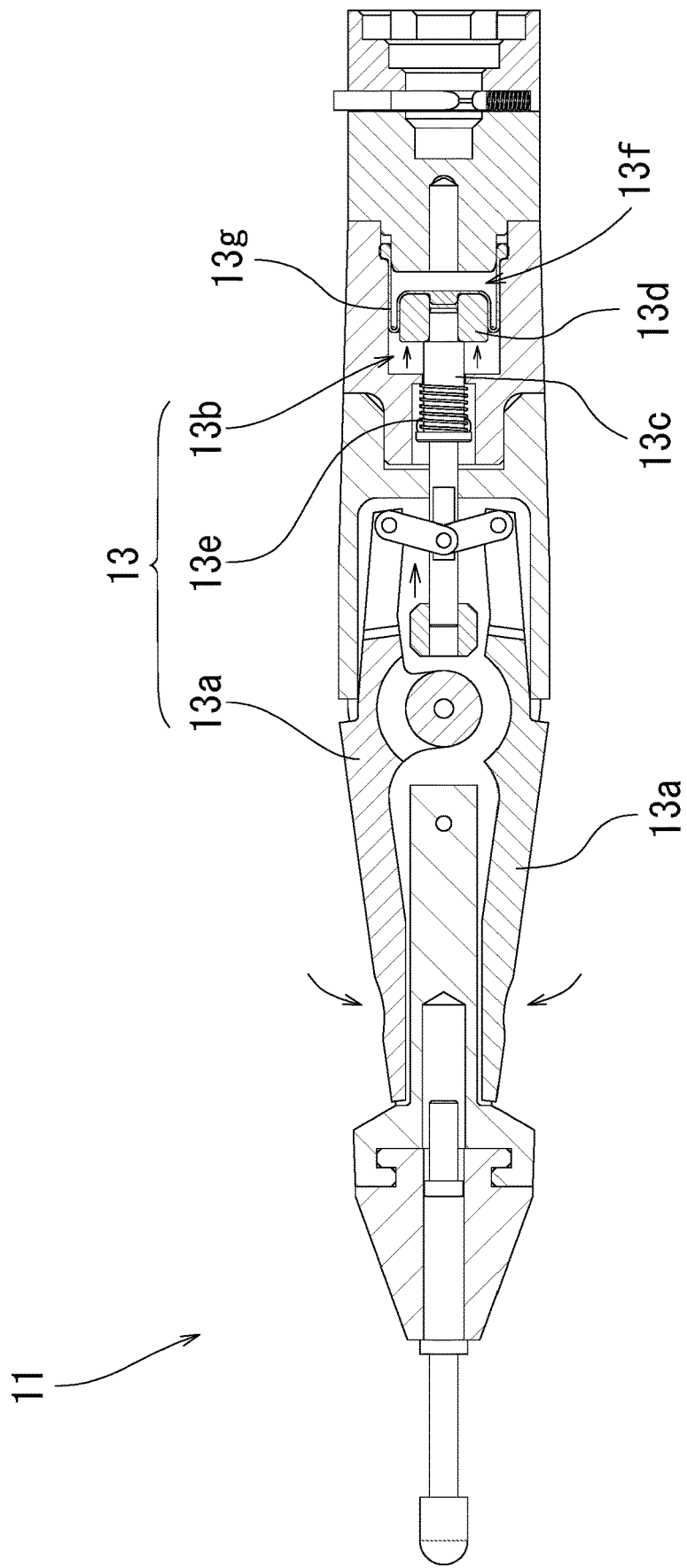
FIG. 4 is an explanatory drawing showing a holding state of the lever parts for the operation input unit in the master unit of the fine work assistance system according to the embodiment of the present invention.

The hydraulic cylinder part 13b changes the fluid pressure of hydraulic fluid in response to a change of the volume of a hydraulic fluid room 13f in a cylinder according to the movement of the piston 13d that reciprocates according to a user operation of the lever parts 13a (see FIGS. 3 and 4). Between the piston 13d and the hydraulic fluid room 13f of the hydraulic cylinder part 13b, a rolling diaphragm 13g is provided that divides the interior of the cylinder into the area of the piston 13d and the hydraulic fluid room 13f while being deformed according to the movement of the piston 13d. The rolling diaphragm 13g keeps a fluid-tight state between the piston 13d and the hydraulic fluid room 13f.

Furthermore, the hydraulic cylinder part 13b of the input mechanism 13 and a predetermined hydraulic driving mechanism 28 provided in the slave unit 20 are connected so as to pass the hydraulic fluid through a pipe 60.

The rolling diaphragm 13g is contained in the hydraulic cylinder part 13b so that the fluid-tight state of the hydraulic fluid room 13f is kept and the piston 13d can smoothly move in the cylinder without resistance. Thus, the user can easily operate the lever parts 13a of the input mechanism 13 with a small force, achieving high operability.

The support mechanism unit 12 has a serial link mechanism with 6 degrees of freedom in which multiple links 12a are connected to one another via joints with 1 degree of freedom so as to accept rotations relative to other adjacent links. The support mechanism unit 12 supports the operation input unit 11 while accepting free positioning and a changing orientation at least in a predetermined range wider than the end-effector movable range of the slave unit 20. Each of the joints between the links of the support mechanism unit 12 has an encoder unit 12b that detects the amount of relative rotation as the sensor for each of the links and a braking unit 12c that optionally generates a braking force as a reaction force according to the operating force of the user.

With this configuration, the support mechanism unit 12 movably supports the operation input unit 11 with 6 degrees of freedom like the parallel link mechanism of the slave unit 20, which will be described later. Moreover, the support mechanism unit 12 can acquire information on the position and orientation of the operation input unit 11 set according to the degree of freedom, as the output signals of the encoder units 12b. Thus, when the user operates the operation input unit 11, the control unit 50 controls the activation of actuators so as to place an end effector 22 of the slave unit 20 in a target position and orientation based on the output signals of the encoder units 12b. Moreover, in this mechanism, the actuators are activated so as to move the end effector 22 to a desired position and orientation according to a change of the position and orientation of the operation input unit 11.

Furthermore, along with the encoder units 12b, the support mechanism unit 12 includes the braking unit 12c (see FIG. 2) at each of the joints connecting the links 12a, the braking unit 12c being capable of generating a braking force against an operating force for moving the operation input unit 11 by the user. Specifically, the braking unit 12c generates a relative force in a direction that suppresses the relative rotation of the link 12a at each of the joints such that the operation input unit 11 is moved by an operation. The braking unit 12c includes, for example, a combination of a known electromagnetic clutch and damper. The damper is typically separated from the joint but is connected to the joint by energizing a clutch, so that braking by the damper is caused to act on the relative rotation between the links.

In this mechanism, the end effector 22 operates in response to a user operation for moving the operation input unit 11; meanwhile, when the end effector 22 of the slave unit 20 moving in response to the user operation reaches a movable limit position based on the mechanical restrictions of links 23 or a linear actuator 24, the control unit 50 having detected and determined the end effector 22 activates the braking unit 12c in response to a continuous user operation for further moving the operation input unit 11 to an area outside the movable limit of the slave unit, thereby applying the braking of the damper as a load resistance. The braking notifies the user who operates the operation input unit 11 that the end effector 22 should not be moved any more. This can prevent the user from performing an unnecessary operation, e.g., further movement of the operation input unit 11, thereby improving the efficiency of operations.

Figure 5:
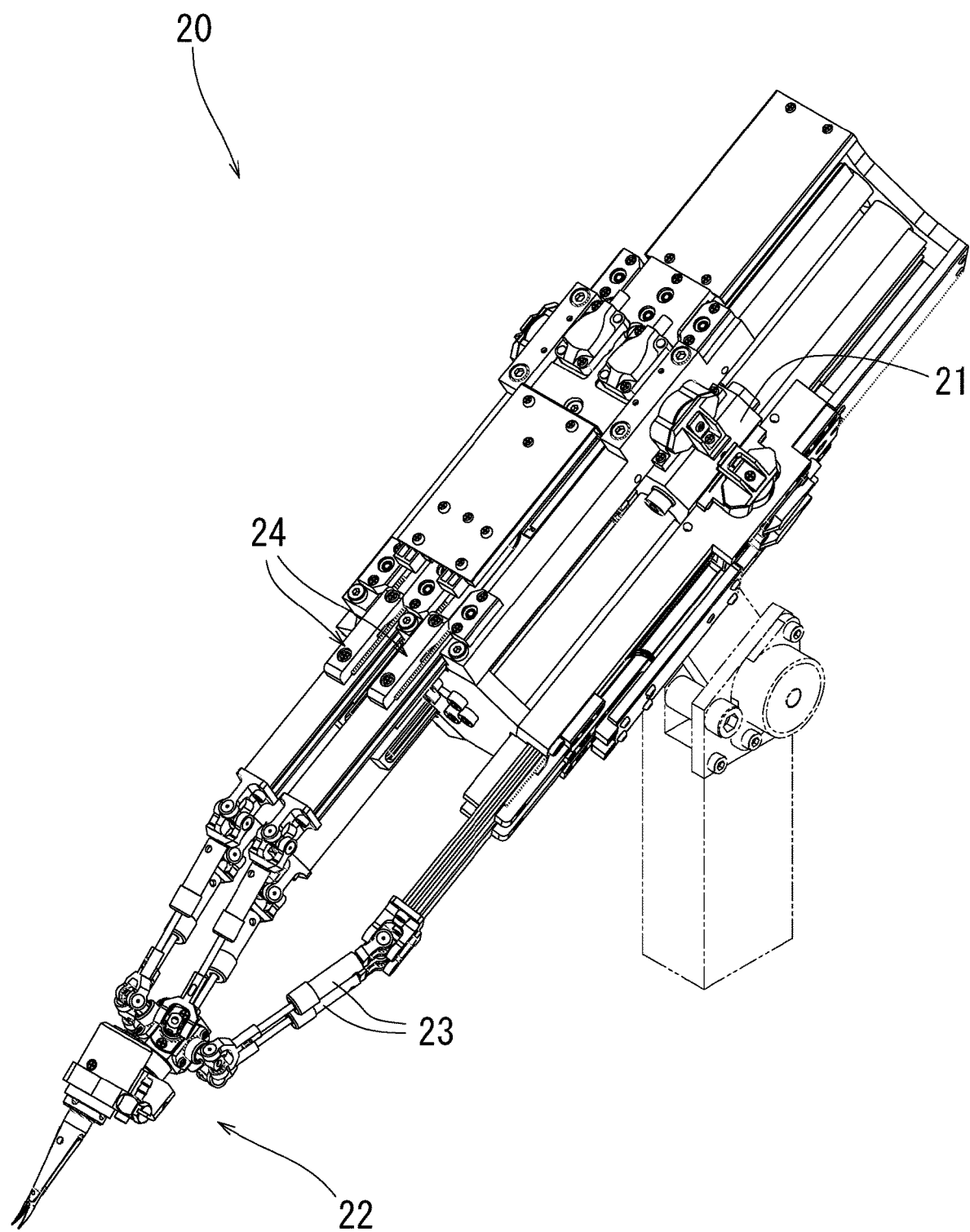
FIG. 5 is a schematic perspective view showing a slave unit in the fine work assistance system according to the embodiment of the present invention.
Figure 6:
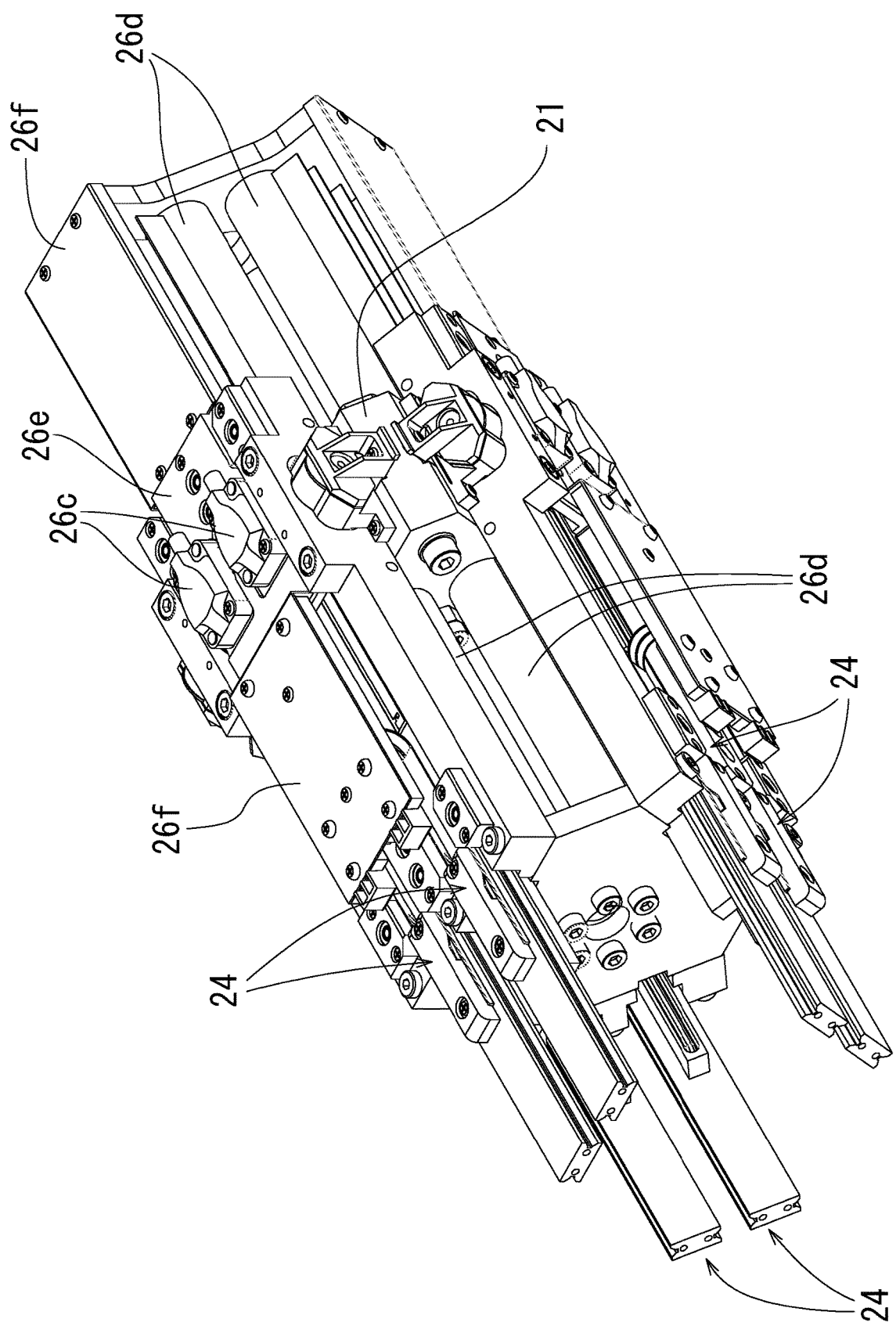
FIG. 6 is a schematic perspective view showing linear actuators in the slave unit of the fine work assistance system according to the embodiment of the present invention.

The slave unit 20 includes a base 21 that is supported via a stand or the like in a predetermined location in a space where a surgery object is present, the end effector 22 that handles a surgery object or a surgical instrument, the six links 23 that are disposed in parallel between the base 21 and the end effector 22, and the six linear actuators 24 that are supported by the base 21 so as to move the links 23 (see FIG. 5).

The base 21, the end effector 22, the links 23, and the linear actuators 24 that constitute the slave unit 20 have a parallel link mechanism with 6 degrees of freedom, in which the linear actuators 24 linearly move the ends of the links 23 so as to move the end effector 22 connected to the other ends of the links.

The parallel link mechanism can change the position and orientation of the end effector 22, which handles a surgery object or a surgical instrument, in a predetermined range relative to the base 21. Since the parallel link mechanism has 6 degrees of freedom, the end effector 22 on the distal end can make the same motion as being supported with a hand.

Figure 7:
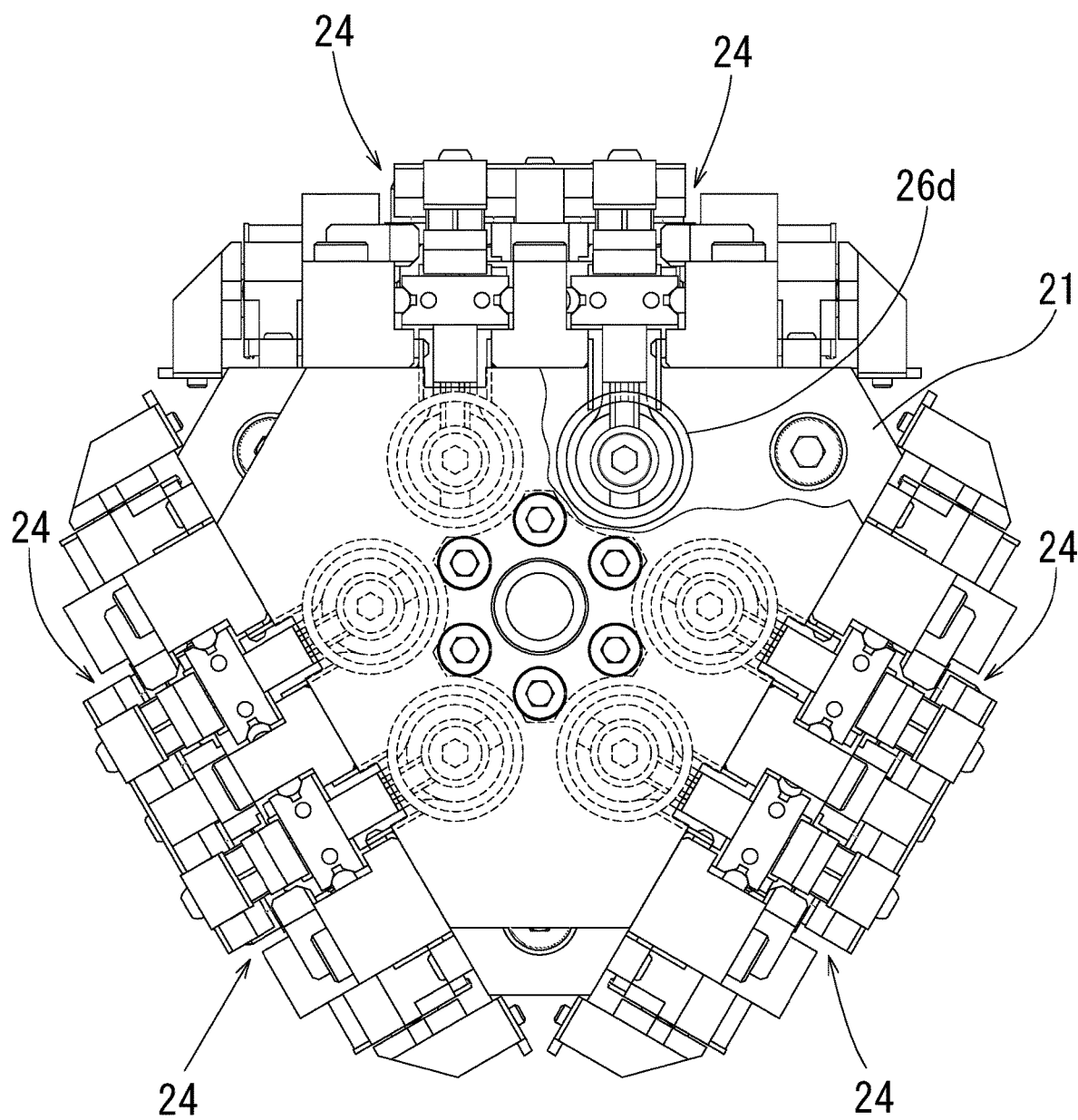
FIG. 7 is a partially cut front view showing the linear actuators in the slave unit of the fine work assistance system according to the embodiment of the present invention.
Figure 8:
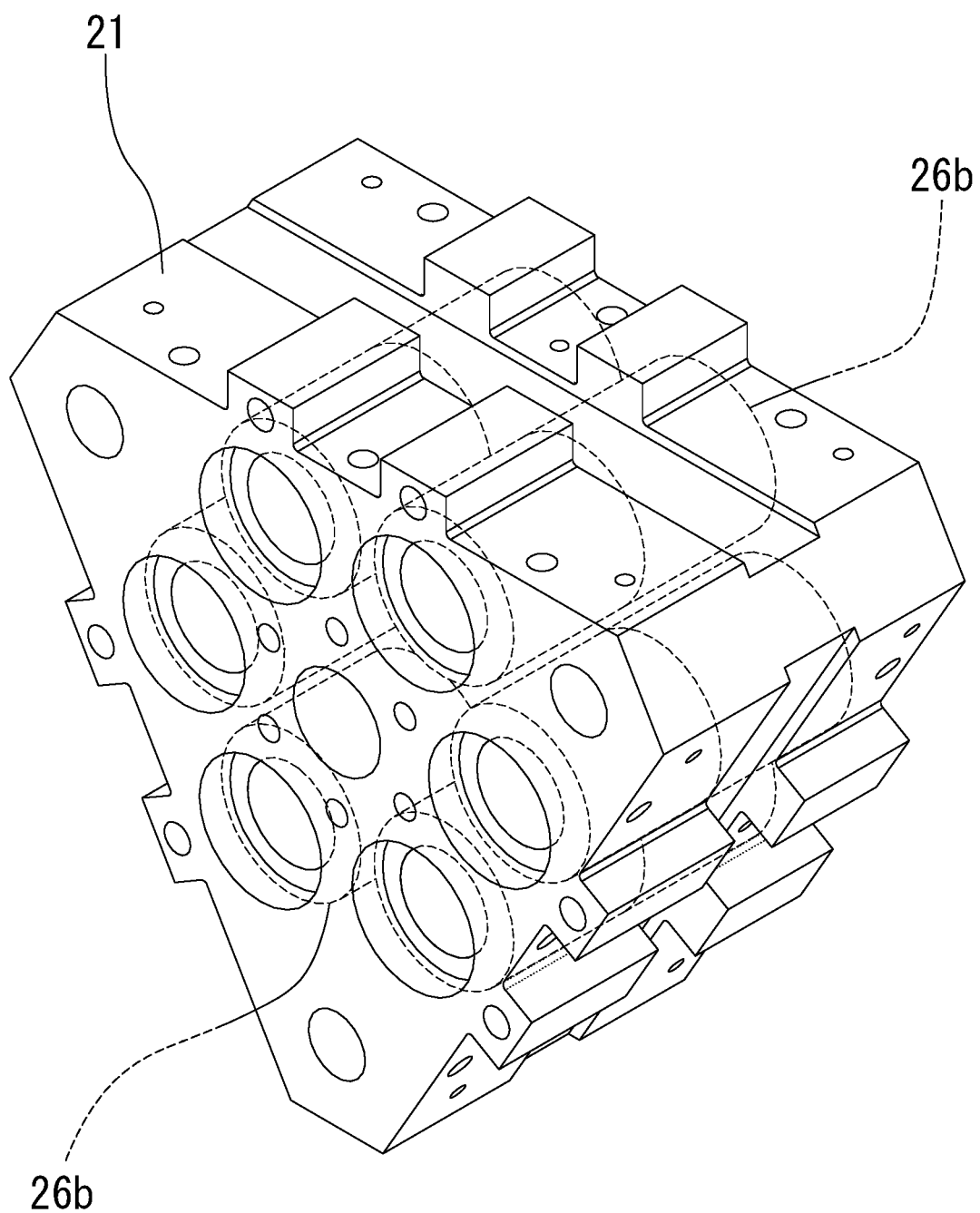
FIG. 8 is a perspective view showing a base in the slave unit of the fine work assistance system according to the embodiment of the present invention.
Figure 9:
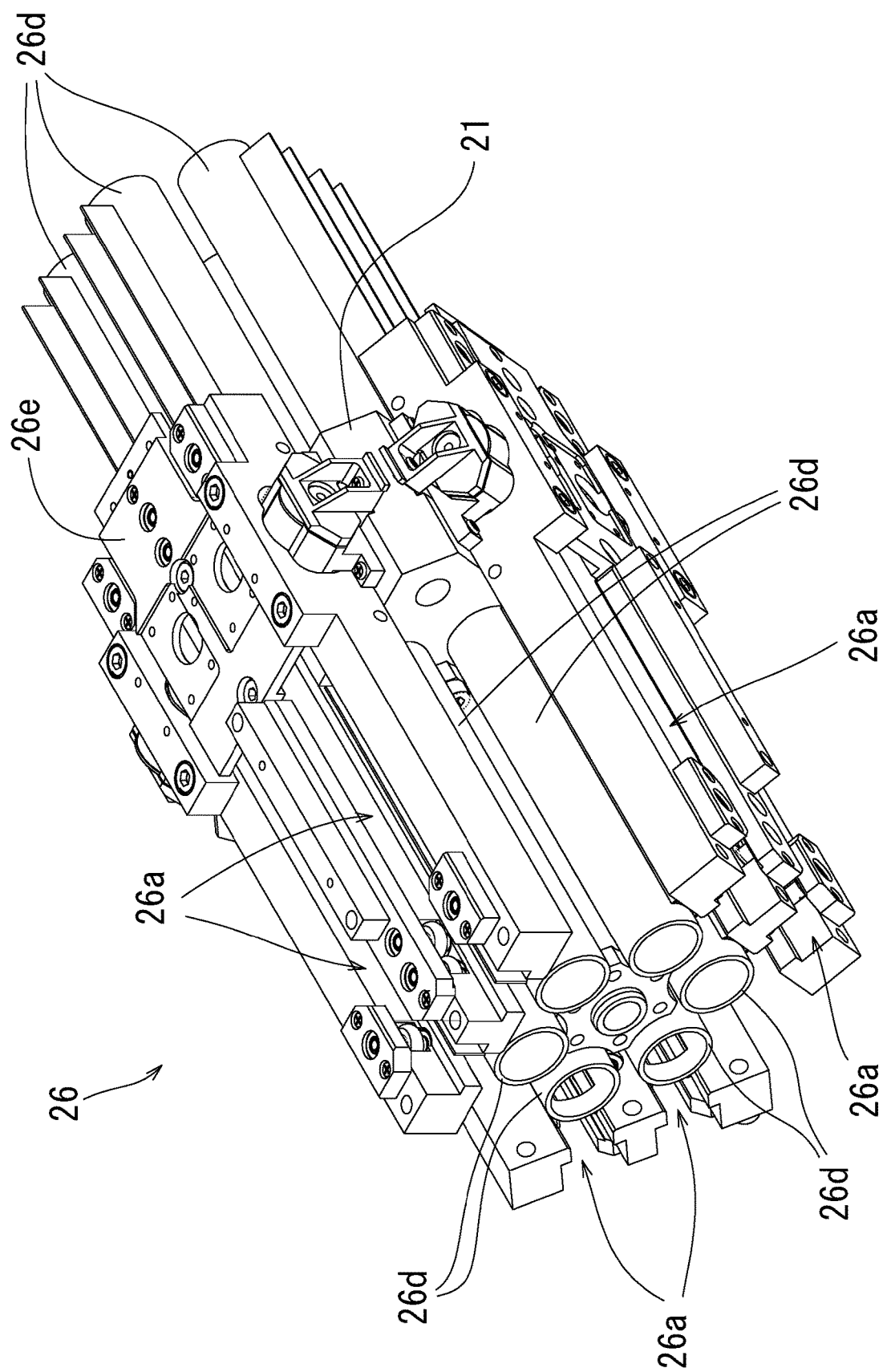
FIG. 9 is a schematic structural diagram showing linear motor stators and magnetic shield members for the linear actuators in the slave unit of the fine work assistance system according to the embodiment of the present invention.

The base 21 is a frame that is substantially triangular in front view (see FIG. 7). Attachment parts for pairs of the linear actuators 24 are provided in three symmetrical locations on the outer surface of the base 21. The base 21 is made of a material possessing high rigidity and can support the movable linear actuators or the like without being affected by, for example, deformation caused by the reaction of the activation of the linear actuators. The base 21 is fixed and supported in the predetermined location in the space where the surgery object is present.

The linear actuator 24 is a moving-coil linear motor configured such that a coil 25b constitutes a part of a mover 25 and a permanent magnet 26b constitutes a part of a stator 26.

Figure 10:
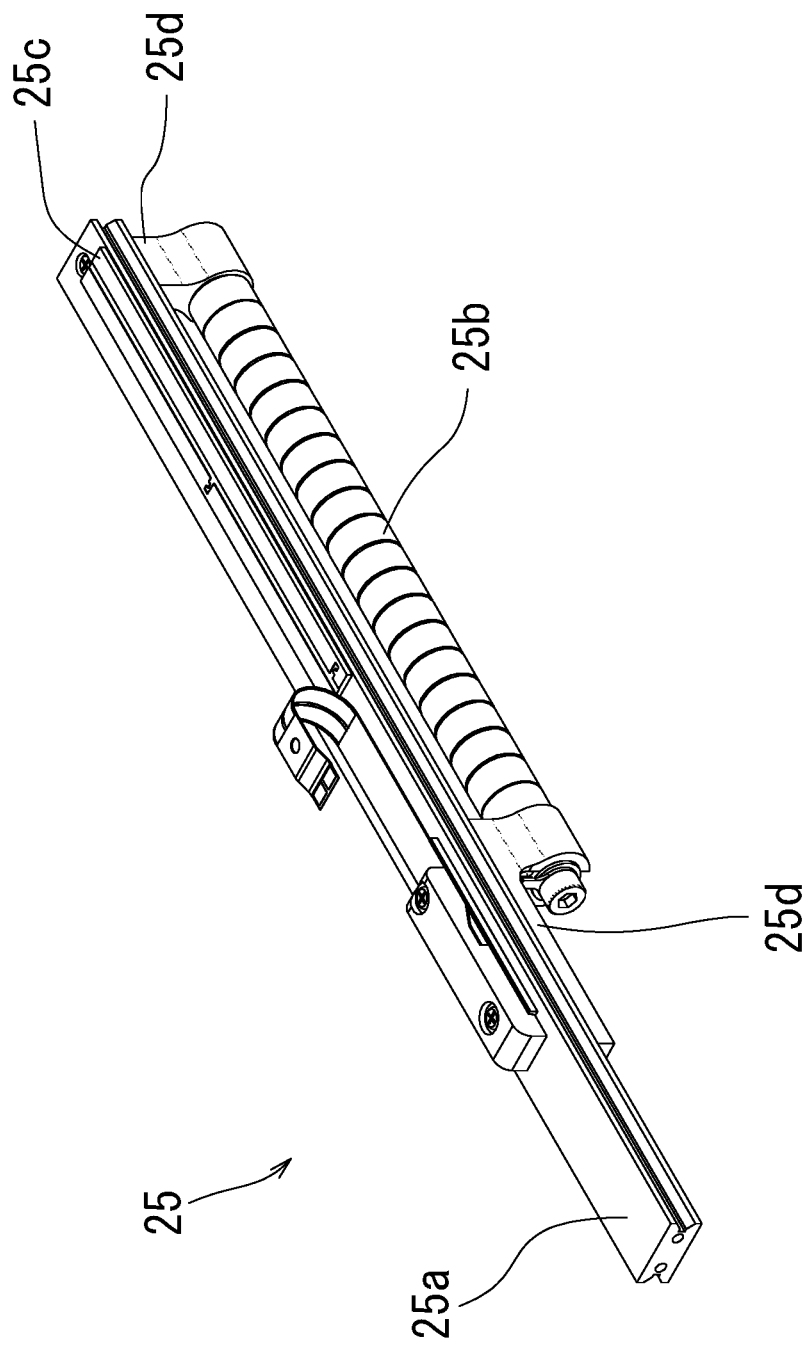
FIG. 10 is a schematic structural diagram showing a linear motor mover for the linear actuator in the slave unit of the fine work assistance system according to the embodiment of the present invention.
Figure 11:
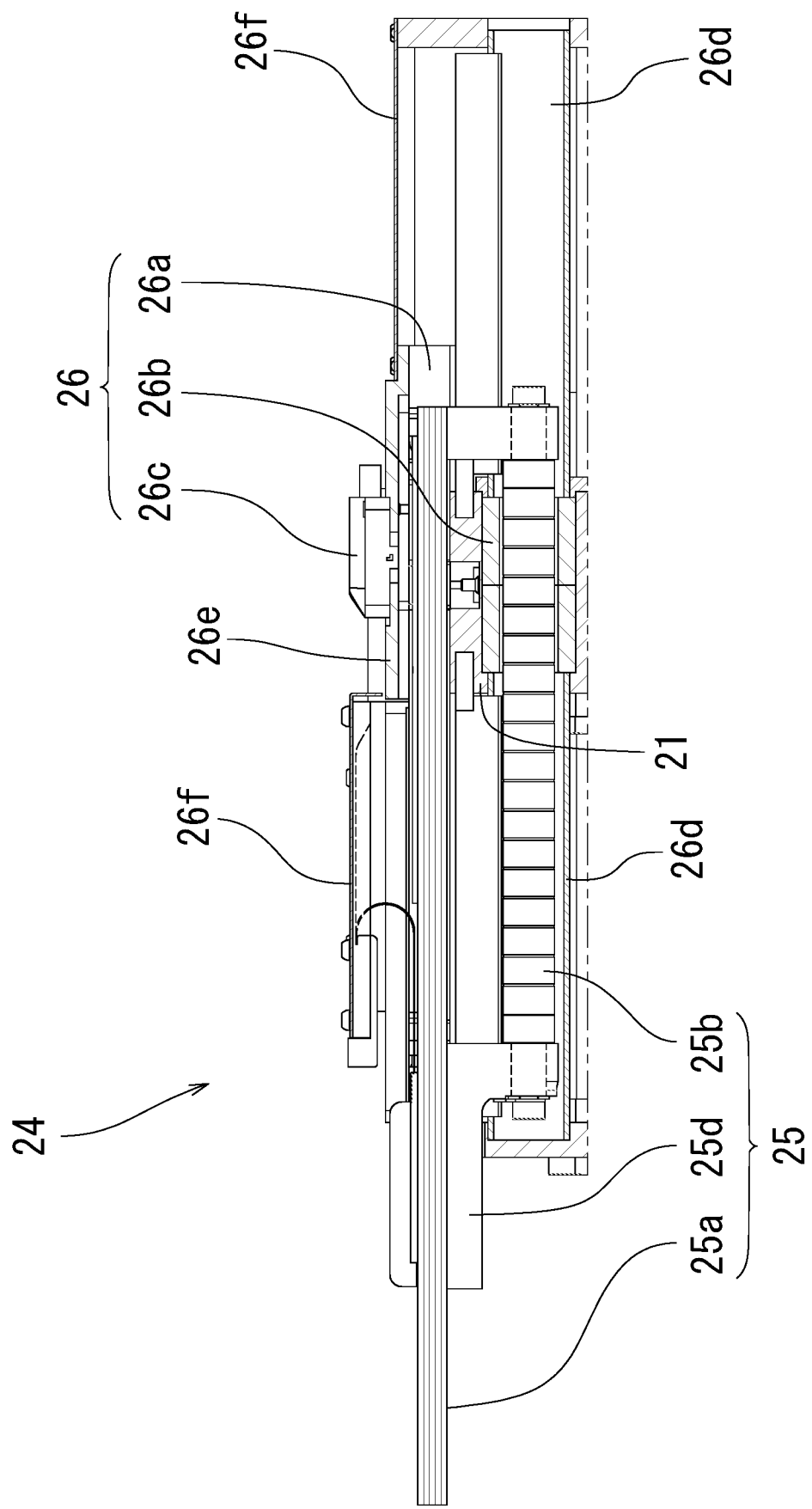
FIG. 11 is an explanatory drawing showing a maximum protrusion of the mover of the linear actuator in the slave unit of the fine work assistance system according to the embodiment of the present invention.
Figure 12:
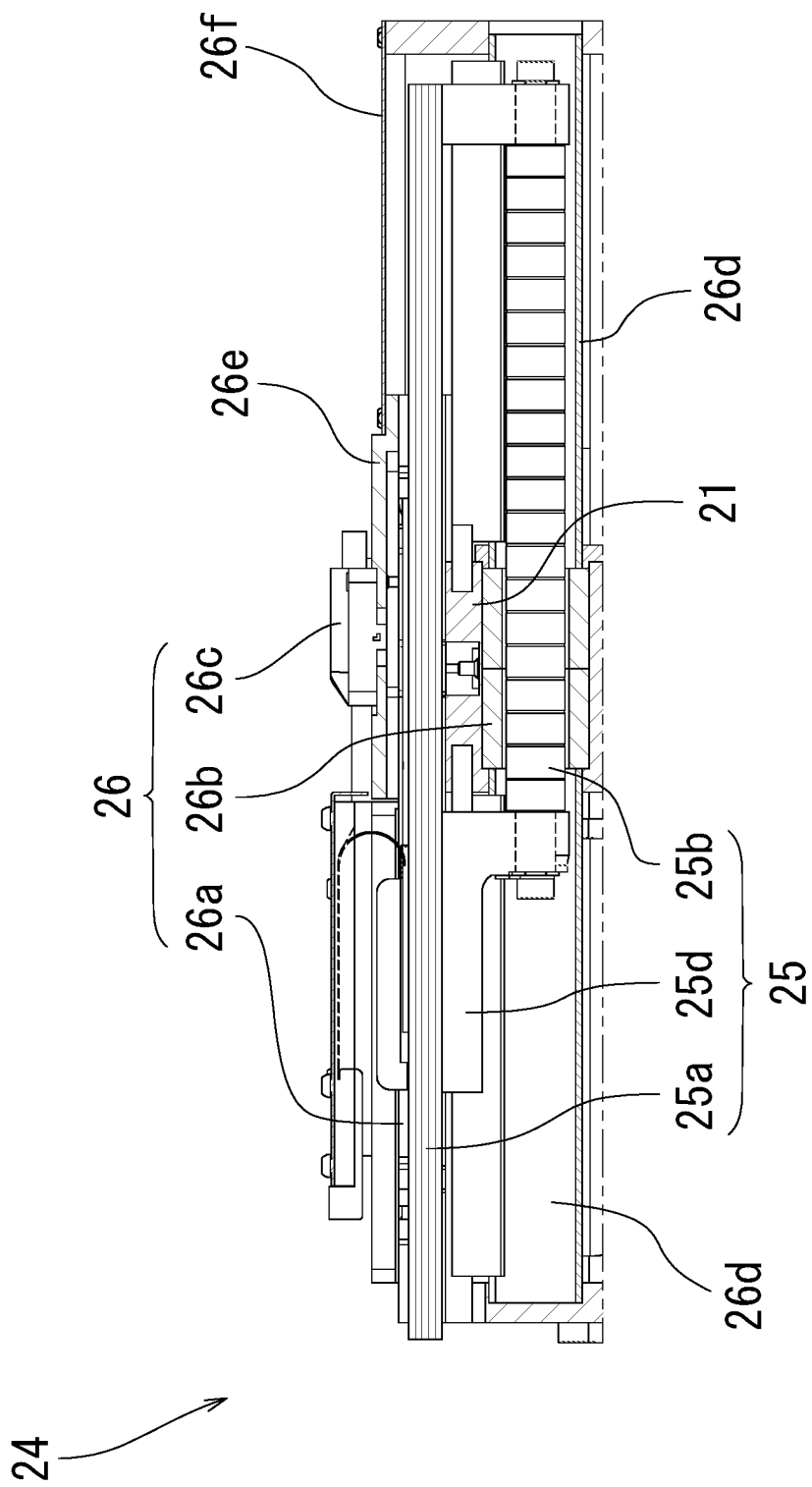
FIG. 12 is an explanatory drawing showing a retracting state of the mover of the linear actuator in the slave unit of the fine work assistance system according to the embodiment of the present invention.
Figure 13:
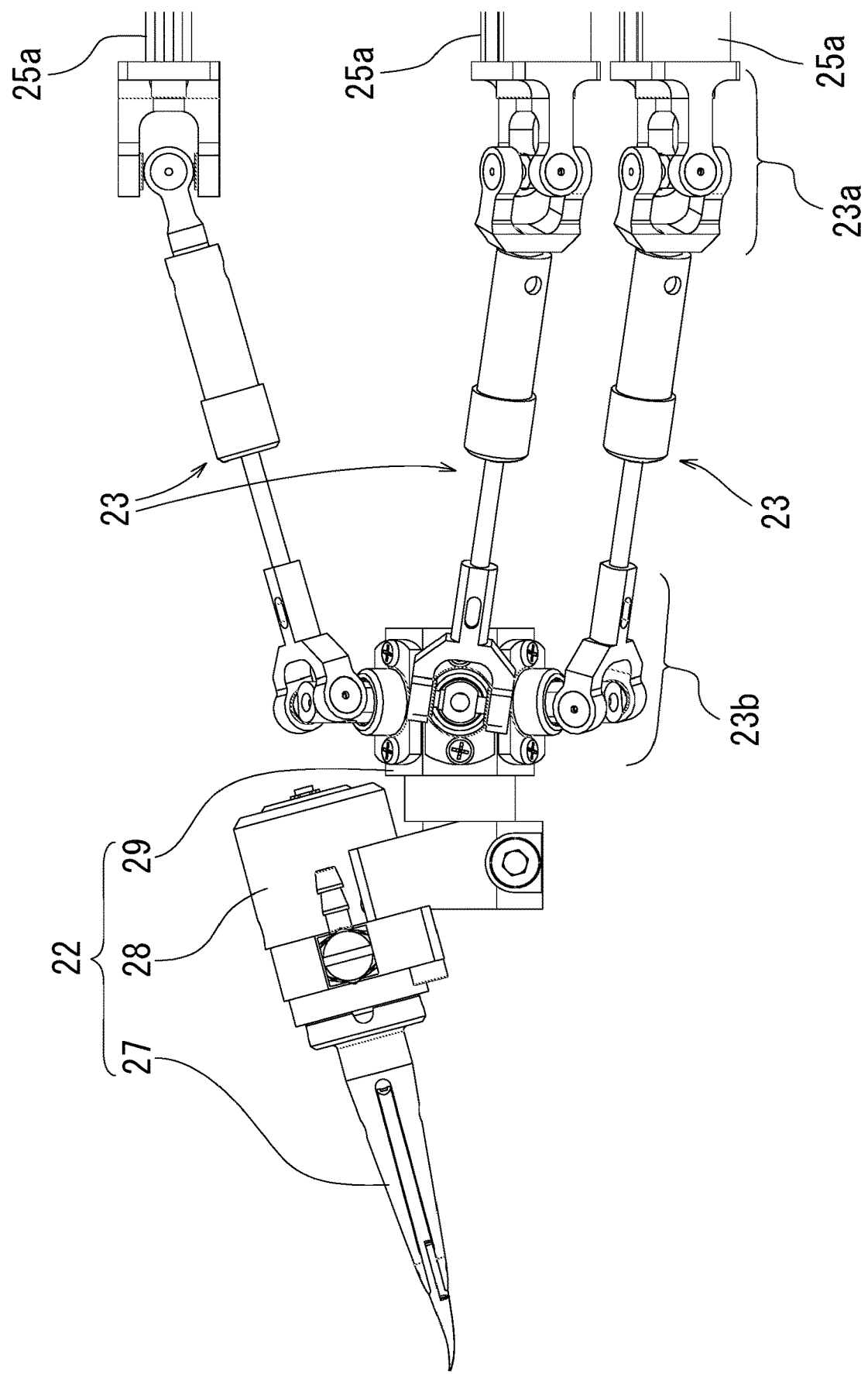
FIG. 13 is a schematic structural diagram showing an end effector and links in the slave unit of the fine work assistance system according to the embodiment of the present invention.
Figure 14:
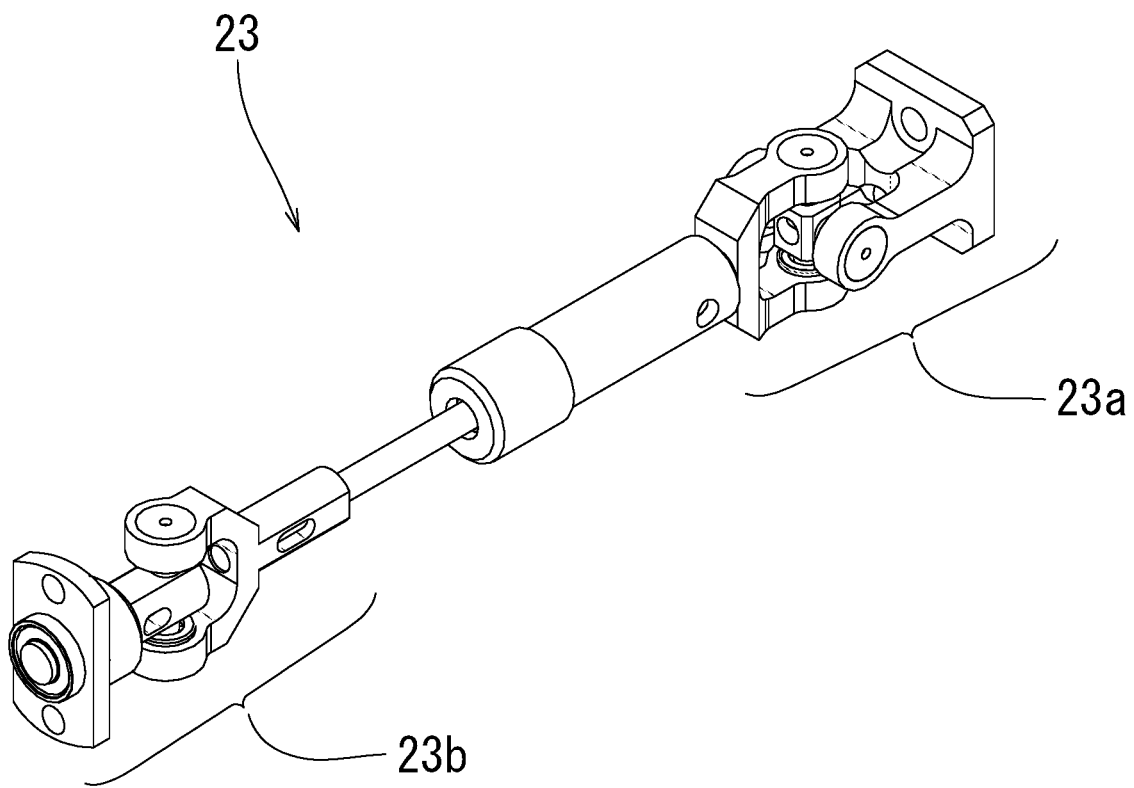
FIG. 14 is a perspective view showing the link in the slave unit of the fine work assistance system according to the embodiment of the present invention.
Figure 15:
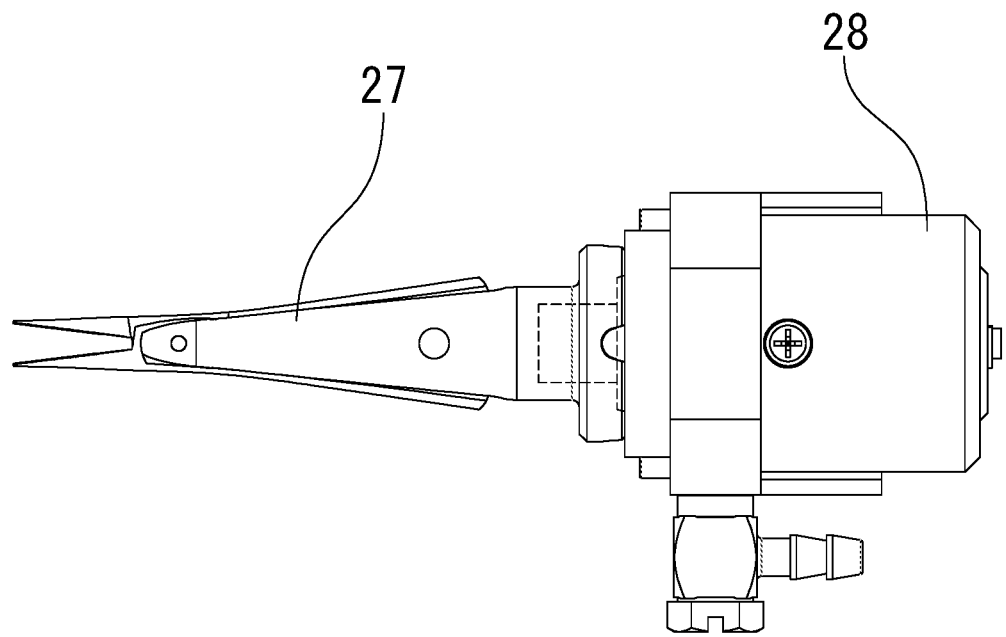
FIG. 15 is an explanatory drawing showing an attached part of a tip operation part for the end effector in the slave unit of the fine work assistance system according to the embodiment of the present invention.
Figure 16:
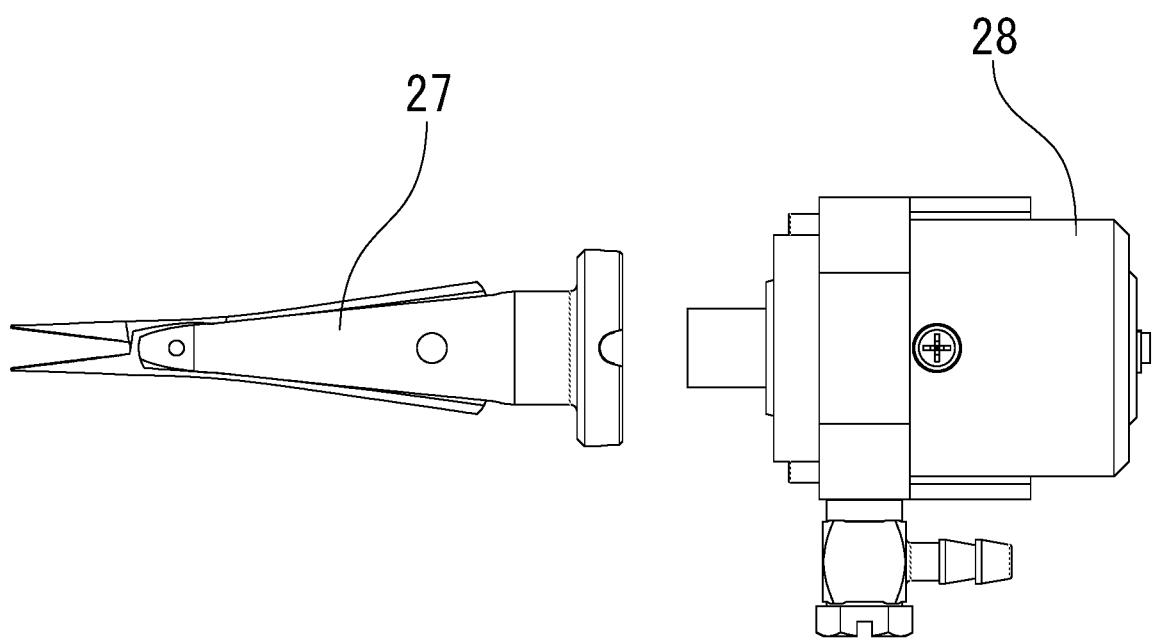
FIG. 16 is an explanatory drawing showing a removed state of the tip operation part for the end effector in the slave unit of the fine work assistance system according to the embodiment of the present invention.

The mover 25 includes a substantially rail-shaped linear-motion slider 25a that is disposed so as to linearly move relative to the base 21, the coil 25b shaped like a small-diameter cylinder integrally attached to the linear-motion slider 25a in a direction parallel to the moving direction of the slider, and a linear scale 25c that is integrally attached to a predetermined part of the linear-motion slider 25a on the opposite side from the attached coil 25b so as to extend in parallel with the moving direction of the slider (see FIG. 10). One end of the link 23 is connected and fixed to the tip end of the linear-motion slider 25a of the mover 25. One end of the link 23 linearly moves with the mover 25 that includes the linear-motion slider 25a.

The stator 26 includes guide parts 26a, each of which is attached to the outer surface of the base 21 while holding the linear-motion slider 25a of the mover 25 via a guide roller or the like so as to linearly move, permanent magnets 26b, each of which is shaped like a cylinder having a larger diameter and a shorter length than the coil 25b and is mounted in the base 21, and sensor parts 26c, each of which is attached to the guide part 26a so as to face the linear scale 25c and detects the movement of the mover as a linear scale displacement.

In the stator 26, the cylindrical permanent magnets 26b (see FIG. 8) mounted in the base 21 are each aligned with the coil 25b of the mover 25 in the cylinder axial direction, the coil 25b movably penetrating the cylinder inner space of the permanent magnet 26b.

Since the linear actuator 24 is a linear motor, a mechanically movable part can be eliminated, contact parts causing sliding and rolling can be reduced, backlash does not occur, the reliability of the mechanism can be improved, and a frictional resistance can be reduced so as to suppress power consumption for driving unlike in other linear-motion mechanisms such as a ball screw.

The actuators 24, each of which is a linear motor including the mover 25 and the stator 26, are parallel to the base 21 in the moving direction of the mover, the permanent magnets 26b of the stator 26 and the coils 25b of the mover 25 are closest to a predetermined virtual center line passing through the center of the base 21 in parallel with the moving direction of the mover, and the permanent magnets 26b and the coils 25b are arranged side by side at regular intervals around the virtual center line.

Additionally, each of the linear actuators 24 includes a magnetic shield member 26d fixed in a predetermined part around the moving path of the coil 25b on both sides of the axial direction of the permanent magnet 26b constituting the stator and over the moving range of the coil. In this mechanism, the magnetic shield member 26d magnetically shields the coil 25b of the mover 25 from the other adjacent coils.

The magnetic shield members 26d are made of magnetic metallic materials such as steel. The cylindrical body of the magnetic shield member 26d is partially cut into a slit. On the edge of the cut portion, a long and thin plate is integrally connected to an edge portion parallel to the axial direction of the cylinder so as to be raised to the outside of the cylinder. The magnetic shield member 26d is extended longer than the coil along the moving path of the coil 25b that linearly move, and has a slit part opened at a location between the coil 25b and the linear-motion slider 25a. The shield member having a partially opened slit can smoothly insert a bracket 25d for connection to the linear-motion slider 25a on the end of the coil 25b while ensuring the shielding for suppressing magnetic influence between the coils. This configuration can integrally move the coil 25b with the linear-motion slider 25a.

The permanent magnet 26b constituting the stator 26 is also close to coils other than the coil 25b that penetrates the cylinder inner space of the permanent magnet 26b and constitutes the pair of linear motors. However, the fixed permanent magnet 26b does not vary magnetic fields unlike the coil 25b and thus does not magnetically affect the movements of the other coils 25b.

Additionally, outside the linear actuators 24 disposed around the base 21, plate-like magnetic shield members 26e and 26f are fixed substantially over the moving ranges of the coils. These magnetic shield members 26e and 26f mainly block fixed magnetic fields generated by the permanent magnets 26b, from the outside. For example, the magnetic shield members 26e and 26f can prevent magnetic instruments such as an injection needle from being sucked to the linear actuators 24.

Regarding the linear motor constituting the linear actuator 24, the coil 25b of the mover 25 is disposed near the virtual center line, the linear-motion slider 25a of the mover 25 is disposed outside the coil 25b, and the linear scale 25c is disposed outside the linear-motion slider 25a. The sensor parts 26c, each of which detects the movement of the mover 25, are disposed on the outermost parts of the actuators 24 and are separated from the coils 25b. Furthermore, the sensor parts 26c are disposed outside the plate-like shield members 26e, thereby suppressing magnetic influence on the sensor parts 26c from the coils 25b and the permanent magnets 26b.

Moreover, the movers 25 and the stators 26 of the linear motors constituting the linear actuators 24 are arranged around the virtual center line, the magnetic shield members 26d are provided around the respective coils 25b, and the magnetic shield members 26e and 26f are disposed outside the magnetic shield members 26d. Thus, the linear actuator parts of the slave unit 20 can collectively reduce leakage flux in a compact structure.

The link 23 is configured such that joints 23a and 23b with multiple degrees of freedom for connection to the linear actuator 24 and the end effector 22 are disposed on the respective ends of a rod body formed by combining two substantially rod-like members that are so rigid as to have resistance to deformation. In the link 23, the substantially rod-like members constituting the rod body are rotatably connected to each other. In this structure, rotational degrees of freedom are set around an axis parallel to the longitudinal direction between a part near one end of the link 23 and a part near the other end of the link 23.

The joint 23a on one end of the link 23 has a structure in which rotational degrees of freedom are set around two intersecting axes. The joint 23a is connected to the end of the linear-motion slider 25a of the linear actuator 24. The joint 23b on the other end of the link 23 has a structure in which rotational degrees of freedom are set around two intersecting axes like the joint 23a. The joint 23b is connected to the end effector 22 (see FIG. 13).

The rotational degrees of freedom are set between the part near one end of the link 23 and the part near the other end of the link 23, and each of the joints 23a and 23b connected on both ends of the link 23 has two rotational degrees of freedom. Thus, the orientation of the link 23 can be freely changed with respect to the linear actuator 24 and the end effector 22 that are connected to the link 23, as in the case of connection via spherical joints. The link mechanism including the link 23 between the linear actuator 24 and the end effector 22 is used for the parallel link mechanism in which the six links 23 are arranged in parallel. Thus, with respect to the base 21, various motions caused by changing the position and orientation of the end effector 22 are accepted with 6 degrees of freedom, the sum of 3 degrees of freedom for movements in three axial directions orthogonal to one another and 3 degrees of freedom of rotations around the three axes, as in the case of supporting the end effector 22 by a human hand.

The end effector 22 is connected to the joints 23b on the other ends of the six links 23 and is movably supported so as to handle a surgery object or a surgical instrument. Specifically, the end effector 22 includes a tip operation part 27 that handles a surgery object or a surgical instrument with opening and closing motions produced with 1 degree of freedom in addition to the motion of the overall parallel link mechanism, the hydraulic driving mechanism 28 that produces motions for handling a surgery object or a surgical instrument with the tip operation part 27, and a joint connecting part 29 that is connected to the other ends of the six links 23 constituting the parallel link mechanism (see FIG. 13).

In this configuration, the tip operation part 27 is detachably attached to the hydraulic driving mechanism 28 (see FIGS. 15 and 16) and can be replaced with another separately from the joint connecting part 29 connected to the other ends of the links 23 and the hydraulic driving mechanism 28 integrated with the joint connecting part 29.

In this way, in the end effector 22, only the tip operation part 27 that actually handles a surgery object or a surgical instrument can be easily replaced with another according to the surgery object or the situation, achieving a mechanism for efficient works for surgery.

Specifically, the tip operation part 27 is substantially conical with two distal ends formed as forceps that are opened and closed so as to hold a surgery object or a surgical instrument. The tip operation part 27 is detachably attached to the hydraulic driving mechanism 28. The tip operation part 27 has a rod portion 27a that can linearly move in synchronization with the opening and closing forceps. The rod portion 27a is moved by the hydraulic driving mechanism 28 so as to open and close the forceps.

The replaceable tip operation part 27 of the end effector 22 is, for example, scissors, tweezers, a needle holder, bipolar coagulation instruments (high-frequency energizing coagulation instruments), and disposable forceps. Additionally, during works for surgery, the tip operation part may be, for example, an electric knife (so-called monopolar coagulation instrument) that is movable in the motion of the overall end effect by the linear actuator and does not need to be separately activated by the hydraulic driving mechanism, used by replacement.

Figure 17:
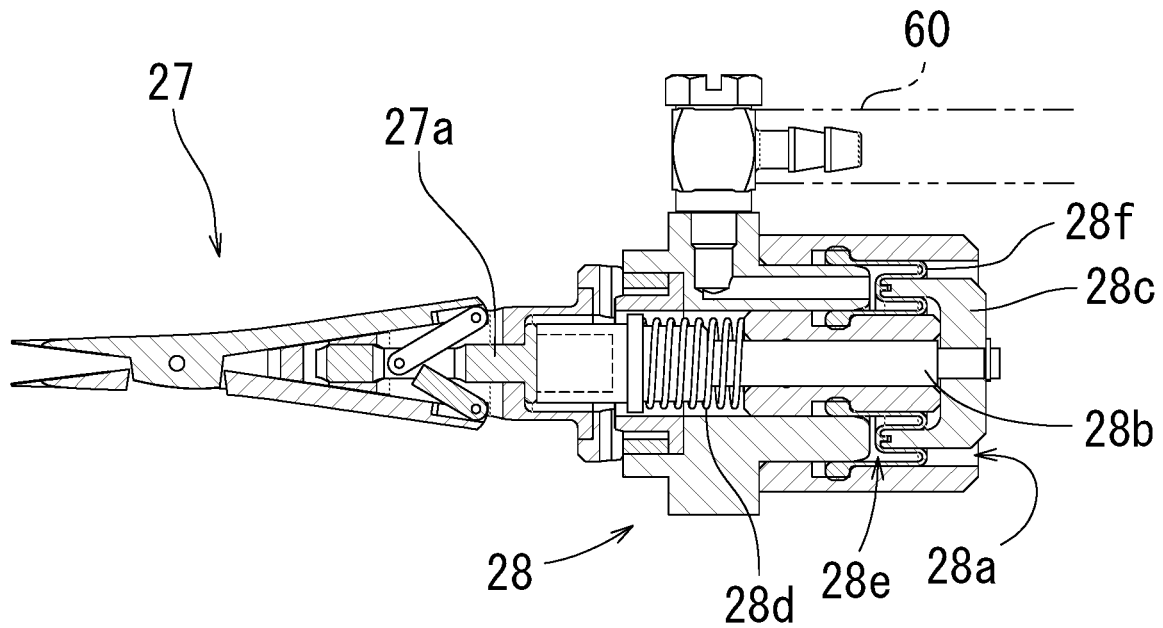
FIG. 17 is an explanatory drawing showing an opened state of forceps on the end effector tip operation part in the slave unit of the fine work assistance system according to the embodiment of the present invention.
Figure 18:
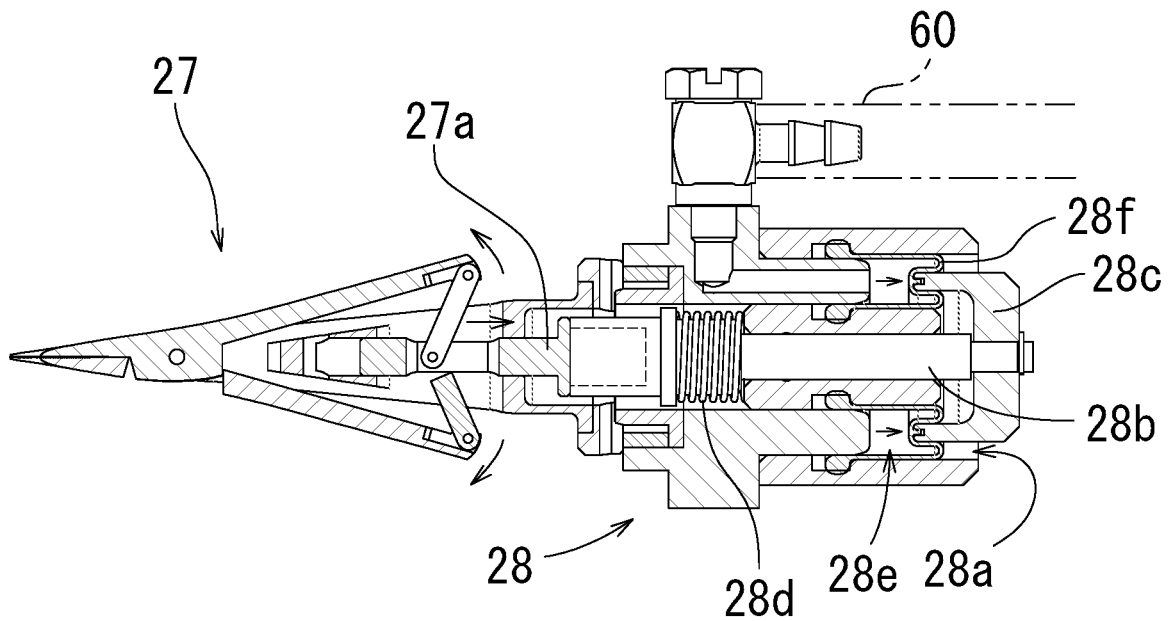
FIG. 18 is an explanatory drawing showing a closed state of the forceps on the end effector tip operation part in the slave unit of the fine work assistance system according to the embodiment of the present invention.
Figure 19:
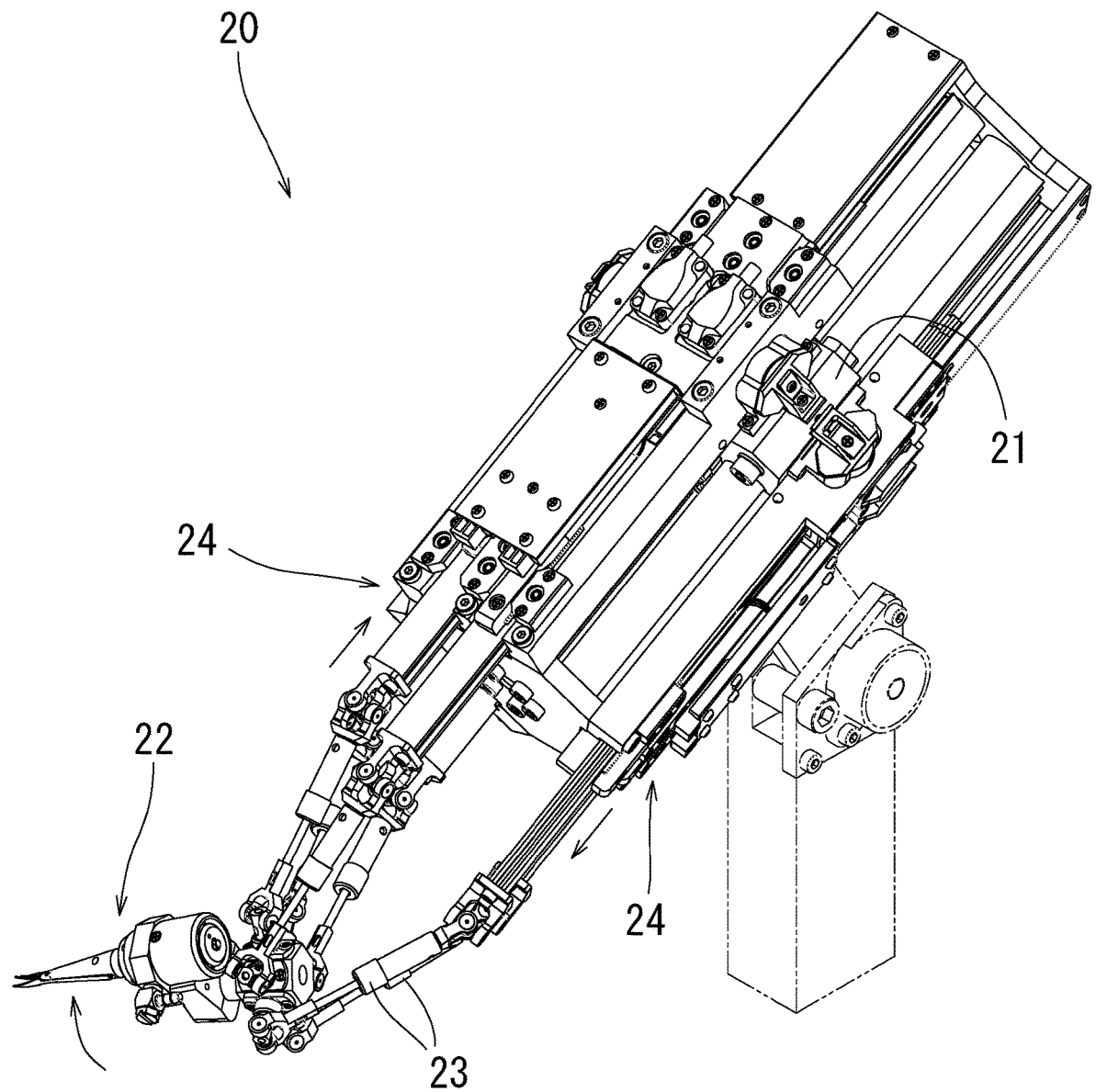
FIG. 19 is an explanatory drawing showing an adjusting operation in a first direction of the end effector in the slave unit of the fine work assistance system according to the embodiment of the present invention.
Figure 20:
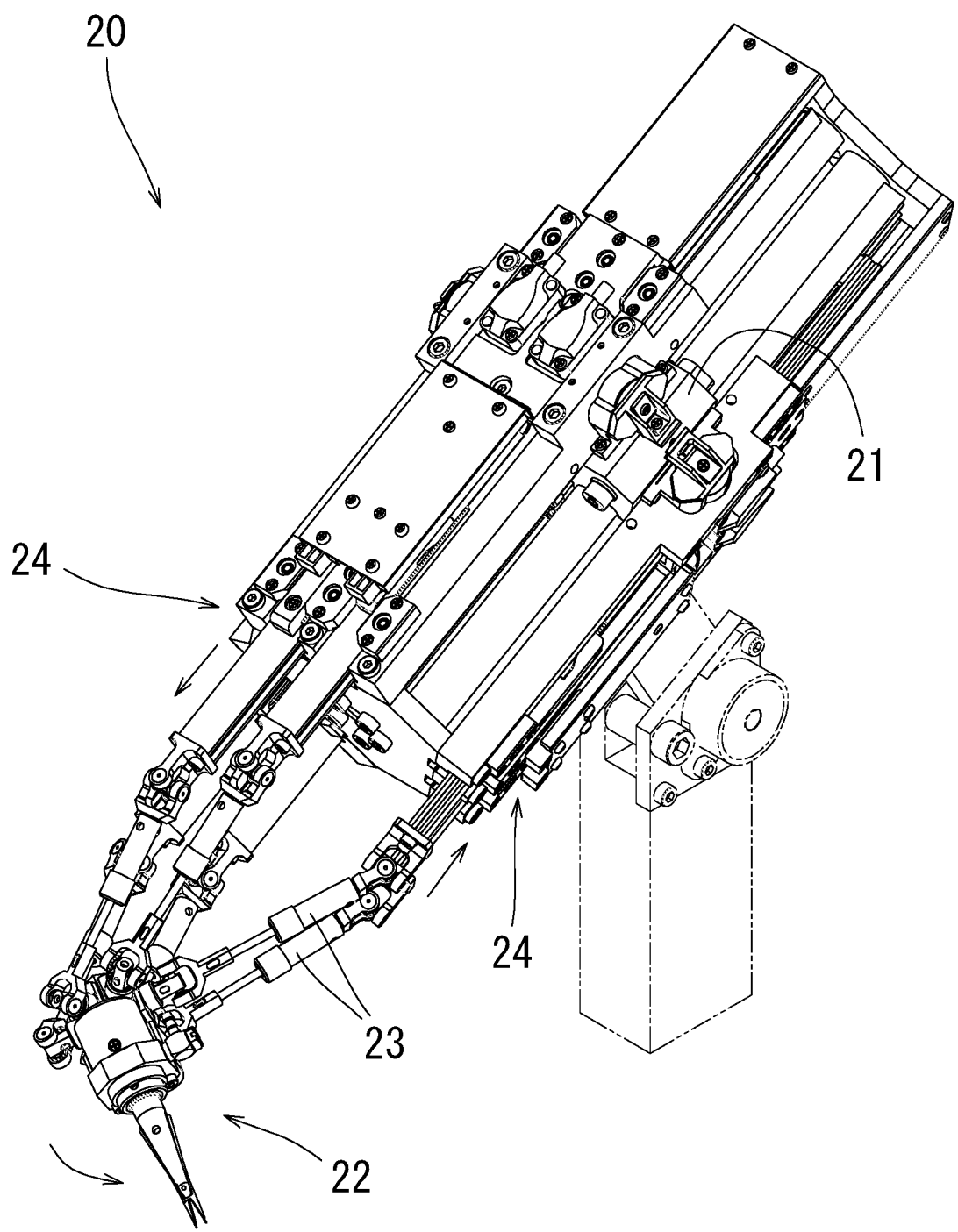
FIG. 20 is an explanatory drawing showing an adjusting operation in a second direction of the end effector in the slave unit of the fine work assistance system according to the embodiment of the present invention.

The hydraulic driving mechanism 28 includes a hydraulic cylinder part 28a that reciprocates a rod 28b and a piston 28c according to a change of the fluid pressure of hydraulic fluid while the rod 28b and the piston 28c are supported so as to linearly move, and a spring 28d that is contained in the hydraulic driving mechanism 28 so as to be compressed according to a fluid pressure increased by supplying hydraulic fluid into the hydraulic cylinder part 28a and so as to urge the rod 28b and the piston 28c back to the original positions with an elastic restoring force when the fluid pressure is restored (see FIGS. 17 and 18). When the tip operation part 27 is attached to the hydraulic driving mechanism 28, the rod 28b of the hydraulic driving mechanism 28 is connected to the rod portion 27a of the tip operation part 27, achieving a mechanism capable of correspondingly transmitting a motion to the forceps of the tip operation part 27 according to a change of the fluid pressure of the hydraulic cylinder part 28a.

The hydraulic cylinder part 28a moves the piston 28c by changing the volume of the hydraulic fluid room 28e in the cylinder according to a change of the fluid pressure of the hydraulic fluid supplied from the outside, and then the hydraulic cylinder part 28a transmits the motion of the piston 28c to the rod portion 27a of the tip operation part 27 through the rod 28b so as to open and close the forceps (see FIGS. 17 and 18). Between the piston 28c and the hydraulic fluid room 28e of the hydraulic cylinder part 28a, a rolling diaphragm 28f is provided that divides the interior of the cylinder into the area of the piston 28c and the hydraulic fluid room 28e while being deformed according to the movement of the piston 28c. The rolling diaphragm 28f keeps a fluid-tight state between the piston 28c and the hydraulic fluid room 28e.

The hydraulic driving mechanism 28 of the end effector 22 connects the hydraulic cylinder part 28a to the hydraulic cylinder part 13b of the input mechanism 13 near the master unit via the pipe 60, allowing the passage of hydraulic fluid. A change of the fluid pressure of the hydraulic fluid in response to a user operation of the input mechanism 13 in the operation input unit 11 is transmitted to the end effector 22 through the pipe, achieving a mechanism for producing motions for handling a surgery object or a surgical instrument through the tip operation part 27.

Additionally, a sheet-type antibacterial cover may be provided over the slave unit except for the tip operation part 27 replaceable with another separately from other parts of the end effector 22. Furthermore, even if the cover is provided, the tip operation part 27 of the end effector may be detachably attached to the hydraulic driving mechanism 28 by using a magnet or the like.

The provision of such a cover securely separates, as a space by the cover, the area of the slave unit other than the tip operation part 27, that is, an area where cleanliness is hardly secured because sterilization is precluded in the presence of various movable mechanisms and current-carrying parts, from an area containing the tip operation part 27 and a surgery object that can be sterilized to secure cleanliness. Thus, cleanliness can be obtained in the area of the surgery object.

The end effector 22 is configured such that the tip operation part 27 is detachably attached to the hydraulic driving mechanism 28. Additionally, the tip operation part 27 and the hydraulic driving mechanism 28 may be handled as a single unit detachably from the joint connecting part 29. The tip end part including the tip operation part and the hydraulic driving mechanism may be replaced with another separately from the joint connecting part that is connected to the other ends of the six links 23 constituting the parallel link mechanism. As described above, the tip operation part is replaced with another along with the hydraulic driving mechanism according to the surgery object and the situation, achieving efficient works for surgery.

The tip operation part does not always need to be detachable. The end effector may have an integral structure including the joint connecting part and the tip operation part.

The imaging unit 30 captures an image of the tip operation part 27 for the end effector of the slave unit 20 and a surgery object. For example, the imaging unit 30 is disposed above the slave unit 20 so as to view the slave unit and the surgery object from above. The imaging unit 30 is a known video camera that can capture high-resolution images while securing reproducibility up to the magnification of a related-art microscope for microsurgery. A detailed description of the imaging unit 30 is omitted.

The display unit 40 optionally enlarges a surgery object image captured by the imaging unit 30 and displays the image for a visual check by the user. The display unit 40 is a known display device, e.g., a liquid crystal display that can display captured images with high resolutions. A detailed description of the display unit 40 is omitted.

Regarding the end effector 22 of the slave unit 20 that moves in response to an operation of the operation input unit 11 of the master unit 10, the user manually operates the operation input unit 11 so as to cause the displayed end effector 22 to perform desired motions while viewing a surgery object and the end effector on the display unit 40.

The control unit 50 receives output signals from the encoder units 12b of the support mechanism unit 12 in a user operation of the operation input unit 11 of the master unit 10, acquires information on the position and orientation of the operation input unit 11 based on the signals, and controls the activation of the linear actuators 24 in the slave unit 20 so as to move the end effector 22 of the slave unit 20 to a desired target position and orientation according to the position and orientation of the operation input unit 11.

Since the activation of the linear actuators 24 is controlled by the control unit 50, the end effector 22 is remotely operated so as to perform the same motion as the operation input unit 11 according to a change of the position and orientation of the operation input unit 11 by a user operation.

Furthermore, the control unit 50 controls imaging by the imaging unit 30 and display on the display unit 40. For example, the control unit 50 may be configured to control imaging and display such that an image of a predetermined range including a surgery object is captured with an appropriate magnification by the imaging unit 30, acquired image information is processed, and the image including the surgery object is displayed to be easily viewed by the user on the display unit 40.

However, imaging by the imaging unit and display on the display unit may not be controlled by the control unit 50. The control unit 50 may control only the activation of the slave unit 20 based on a user operation on the master unit 10.

Moreover, the control unit 50 may be provided as a single control unit separately from the master unit and the slave unit, may be provided along with one of the master unit and the slave unit, or may be separately provided in the master unit and the slave unit.

If the operation input unit of the master unit 10 includes operation means such as an electrical switch other than the input mechanism, the control unit may control the slave unit or other mechanisms into a predetermined activation state in response to an operation.

The control unit 50 is configured such that information on the position and orientation of the operation input unit 11 is acquired as the output signals from the encoder units 12b of the support mechanism unit 12 constituting the serial link mechanism, and the activation of the linear actuators 24 is controlled based on the output signals of the encoder units 12b so as to place the end effector 22 of the slave unit 20 in a position and orientation corresponding to the operation input unit 11. The present invention is not limited to this configuration. For example, the link mechanisms of the master unit 10 and the slave unit 20 are identical parallel link mechanisms, and relative displacements to be detected by the sensors such as an encoder on the links near the master unit are respectively associated with displacements made by the activation of the actuators on the links near the slave unit. In this case, without temporarily acquiring information on the position and orientation of the operation input unit, the control unit may control the activation of the actuators in response to the outputs of the sensors, activate the actuators, and move the links so as to change the end effector to a desired position and orientation.

The operating state of the fine work assistance system according to the present embodiment will be described below.

It is assumed that the slave unit 20 faces a surgery object at a proper distance from the surgery object in an initial state where the end effector 22 does not activate the linear actuator 24, the base 21 is supported and fixed by a support stand or arm or the like, the imaging unit 30 is installed so as to capture an image of the surgery object, and the display unit 40 and the master unit 10 are disposed on a working space, e.g., a desk while the user can operate the master unit 10 while viewing the display unit 40.

In coarse adjustment of, for example, the position of the slave unit 20 relative to a surgery object, a support stand or arm is manually moved and adjusted so as to direct the end effector 22 to the surgery object at a proper distance from the surgery object while the base 21 of the slave unit 20 is attached and supported on the support stand or arm, and in the end, the arm or the like is fixed so as to finally position the slave unit 20. The adjustment is completed thus. A configuration for the adjustment is not a complicated configuration where a predetermined mechanism capable of moving the overall slave unit 20 is operated by the master unit. In the configuration for the adjustment, the master unit 10 is operated only for the motions of the end effector 22 relative to the base 21, so that the configuration is suitable for microsurgery with simplicity and accuracy easily ensured.

The user initially starts the system so as to activate the slave unit 20 according to a change of the orientation and position of the operation input unit 11 in the master unit 10.

Then, while viewing the display unit 40, the user operates the operation input unit 11 such that a desired motion is performed near a surgery object by the end effector 22 of the slave unit 20 corresponding to the operation input unit 11.

When the user moves the operation input unit 11, the output signals from the encoder units 12b of the support mechanism unit 12 are inputted to the control unit 50, and then the control unit 50 acquires the position and orientation of the operation input unit 11. Subsequently, the control unit 50 outputs control signals for controlling the activation of the linear actuators 24 of the slave unit 20, the control signals causing the end effector 22 of the slave unit 20 to perform motions according to a change of the position and orientation of the operation input unit 11.

In the slave unit 20, the linear actuators 24 are activated based on the control signals outputted from the control unit 50 and move one ends of the links 23. According to the motions of the six links 23 as a result of the linear movements of one ends of the links, the position and orientation of the end effector 22 are changed (see FIGS. 19 and 20).

The control unit 50 controls the activation of the linear actuators 24 for moving one ends of the links 23, so that the end effector 22 is positioned and oriented according to a change of the position and orientation of the operation input unit 11 during the operation.

The user operates the operation input unit 11 so as to place the end effector 22 in a desired position and orientation relative to a surgery object. Additionally, if it is necessary to hold a predetermined point of the surgery object with the tip operation part 27 or hold a surgical instrument such as a needle for anastomosis or suture, the user holds with fingers the pair of lever parts 13a of the input mechanism 13 in the operation input unit 11. Thus, a change of fluid pressure is transmitted from the input mechanism 13 to the hydraulic driving mechanism 28 through the pipe 60, causing the hydraulic driving mechanism 28 to activate the tip operation part 27.

With this configuration, in addition to an operation for changing the position and orientation of the end effector 22 in response to an operation for moving the overall operation input unit 11, the forceps of the tip operation part 27 are moved to hold the predetermined point of the surgery object or the surgical instrument. In the operation for activating the tip operation part 27, a change of predetermined reaction force according to an amount of motion is fed back to the operation input unit 11 as a change of fluid pressure and thus the sense of force is changed on the fingers of the user through the lever parts 13a. This allows the user to roughly feel how the forceps of the tip operation part 27 hold the predetermined point of the surgery object or the surgical instrument, with fingers operating the input mechanism 13.

The user operates the input mechanism 13 in this way, so that the tip operation part 27 of the end effector 22 is moved so as to hold or release a blood vessel or the like of a surgery object or hold or release a surgical tool such as a needle. Along with an operation for moving the overall operation input unit 11 while viewing the display unit 40, for example, a precise work for inserting an anastomosis needle, which is held with the tip operation part 27, into a vascular junction can be performed by properly moving the end effector 22 and the tip operation part 27.

As an input part for a direct operation with fingers in the input mechanism 13, the pair of lever parts 13a is provided at two points opposed to each other on the outer surface of the operation input unit 11. In a manual operation of the overall operation input unit 11 by the user, the lever parts 13a further receive an input operation of holding the lever parts 13a with at least two fingers and changing the holding force of the fingers. The input operation with two fingers holding the pair of lever parts 13a corresponds to a direct manual operation of the forceps of the tip operation part 27. The forceps are actually opened and closed to hold a surgery target or a surgical instrument. Thus, the user can easily understand a correspondence between the operation of the lever parts 13a and the motion of the forceps of the tip operation part 27. The user feels like as if the two distal ends of the forceps of the tip operation part 27 were actually operated and moved with hands. This promotes a proper operation and causes the tip operation part 27 to reliably perform a desired motion.

In this way, in the fine work assistance system according to the present embodiment, a parallel link mechanism with multiple degrees of freedom is used as the link mechanism in which the end effector 22 is movable relative to the base 21 on the fixed side in the slave unit 20 of the master-slave manipulator. Moreover, the end effector 22 is operated by moving one ends of the links by means of the linear actuators 24 supported by the base 21, the linear actuators 24 of the slave unit 20 are activated and the position and orientation of the end effector 22 are changed in response to a user operation for changing the position and orientation of the operation input unit 11 of the master unit 10. Thus, a precise motion can be achieved for the end effector 22 in the simple and rigid link mechanism where errors are hardly accumulated. Also in a remote operation by a user who is viewing a captured image on the display, operations for microsurgery can be performed by the end effector 22. The same motions can be reproduced as the techniques of skilled doctors and workability can be improved to reduce the burden of the user.

In the end effector 22 of the manipulator constituting the slave unit 20, the tip operation part 27 for actually handling a surgery object or a surgical instrument is activated by hydraulic driving, a user operation for the input mechanism 13 in the operation input unit 11 on the master side is transmitted as a change of fluid pressure to the end effector 22, and then the tip operation part 27 is operated. Thus, through hydraulic fluid flowing between the operation input unit and the end effector, the tip operation part 27 can be operated by a driving force substantially proportionate to the operating force of the user, a reaction force applied to the tip operation part 27 can be fed back to the input mechanism through a hydraulic transmission system, the user can handle a surgery object or a surgical instrument without applying an excessive force to the surgery object or the surgical instrument through the tip operation part 27 while properly feeling the tip operation part 27 in contact with any object from the sense of operation of the input mechanism 13, thereby achieving high operability and safe work for surgery. The tip operation part 27 is hydraulically driven and thus does not need to be provided with a sensor for detecting a force unlike in motor driving. This can eliminate the need for a complicated work, e.g., calibration of a sensor, reduce the size of the end effector 22, and easily sterilize the end effector 22 in use for surgery.

In the fine work assistance system according to the embodiment, as an input part in the operation input unit 11 of the master unit 10, the tip operation part 27 of the end effector 22 is shape like forceps with two distal ends operating so as to hold a surgery object or a surgical instrument. Accordingly, the pair of lever parts 13a is provided at two points opposed to each other on the outer surface of the operation input unit 11. In a manual operation of the overall operation input unit 11 by the user, the lever parts 13a further receive an input operation of holding the lever parts 13a with at least two fingers and changing the holding force of the fingers. In a holding operation with fingers in response to a motion of the tip operation part of the end effector, the following configuration may be used: the operation input unit has an input part in one location, one finger is in contact with the input part, whereas the other finger is in contact with a predetermined point on the outer surface of the operation input unit so as to be opposed to the one finger. Although the operation input unit is held with the fingers, the input part needs to be moved by only one of the fingers, whereas the other finger is actually fixed.

In the fine work assistance system of the embodiment, a coarse adjustment of, for example, the position of the slave unit 20 relative to a surgery object is made such that a support stand or arm is manually moved and adjusted so as to direct the end effector 22 to the surgery object at a proper distance from the surgery object while the base 21 of the slave unit 20 is attached and supported on the support stand or arm. The present invention is not limited to this coarse adjustment. A moving mechanism for coarse positioning may be provided to automatically make rough adjustment by an operation of the master unit instead of a manual operation. For example, in an operation on the master unit, when the operation input unit reaches an area equivalent to the outside of the movable range of the end effector in response to the activation of the linear actuators, the moving mechanism of the overall slave unit is activated instead of or along with braking caused by activating the braking unit of the master unit, and the end effector is moved with the slave unit in a direction corresponding to the operating direction of the user who is moving the end effector.

REFERENCE SIGNS LIST 1 fine work assistance system
10 master unit
11 operation input unit
12 support mechanism unit
12a link
12b encoder unit
12c braking unit
13 input mechanism
13a lever parts
13b hydraulic cylinder part
13c rod
13d piston
13e spring
13f hydraulic fluid room
13g rolling diaphragm
20 slave unit 21 base
22 end effector
23 link
23a, 23b joint
24 linear actuator
25 mover
25a linear-motion slider
25b coil
25c linear scale
25d connecting bracket
26 stator
26a guide part
26b permanent magnet
26c sensor part
26d magnetic shield member
26e, 26f magnetic shield member
27 tip operation part
27a rod portion
28 hydraulic driving mechanism
28a hydraulic cylinder part
28b rod
28c piston
28d spring
28e hydraulic fluid room
28f rolling diaphragm
29 joint connecting part
30 imaging unit
40 display unit
50 control unit
60 pipe

The invention claimed is:

1. A fine work assistance system comprising a master-slave manipulator, in which a slave unit performs a predetermined operation for fine work on a work object in response to input of a user operation to a master unit of the manipulator,
the fine work assistance system comprising:
an imaging unit that captures an image of the work object; and
a display unit that enlarges the work object image captured by the imaging unit and displays the image for a visual check by a user,
wherein the slave unit has a parallel link mechanism with at least 3 degrees of freedom, the parallel link mechanism including a base that is supported in a predetermined location in a space where the work object is present, an end effector that handles the work object or a work instrument, and a plurality of links that are disposed in parallel between the base and the end effector, the parallel link mechanism being capable of changing a position and orientation of the end effector in a predetermined range relative to the base,
wherein the parallel link mechanism includes a plurality of linear actuators supported by the base, each linearly moving one end of the link and moving the end effector connected to the other end of the link,
the end effector includes a tip operation part that handles the work object or the work instrument with at least 1 degree of freedom in addition to a motion of the overall parallel link mechanism different from that of the end effector, and a hydraulic driving mechanism that produces a motion for handling the work object or the work instrument by the tip operation part,
the master unit includes an operation input unit that receives a user operation, and a support mechanism unit that is capable of acquiring information on a position and orientation of the operation input unit while movably supporting the operation input unit with the same degree of freedom as the parallel link mechanism,
the operation input unit has an input mechanism that changes a fluid pressure of hydraulic fluid in response to a predetermined user operation independent of an operation for moving the overall operation input unit, the input mechanism being connected to the hydraulic driving mechanism in the end effector of the slave unit so as to pass the hydraulic fluid through a pipe, and
the hydraulic driving mechanism activates the tip operation part in response to a change of a fluid pressure of hydraulic fluid by a user operation on the input mechanism in the operation input unit.

2. The fine work assistance system according to claim 1, wherein the linear actuator of the slave unit is a moving-coil linear motor configured such that a coil constitutes a part of a mover and a permanent magnet constitutes a part of a stator,
the mover includes a linear-motion slider that is disposed so as to linearly move relative to the base, and the coil that is shaped like a cylinder integrally attached to the linear-motion slider, the coil being disposed with an axial direction parallel to a moving direction of the slider, and
the stator includes a cylindrical permanent magnet shorter than the coil, the permanent magnet being fixed to the base so as to be aligned with the coil in a cylinder axial direction, the coil movably penetrating the cylinder inner space of the permanent magnet.

3. The fine work assistance system according to claim 2, wherein the linear motors serving as the linear actuators are disposed in parallel in a moving direction of the mover, the coil of the mover is disposed on the base around a predetermined virtual center line extending in parallel with the moving direction of the mover such that the coil is closest to the virtual center line,
each of the linear motors includes a magnetic shield member which has a predetermined cross-sectional shape and is disposed around the coil and over a movable range of the coil, and at least the coil is shielded from other coils by the magnetic shield member.

4. The fine work assistance system according to claim 1, wherein the parallel link mechanism of the slave unit is a mechanism with at least 6 degrees of freedom in which the linear actuators and the at least six links are disposed in parallel.

5. The fine work assistance system according to claim 1, wherein the end effector of the slave unit has a predetermined range part including the tip operation part such that at least the predetermined range part is replaceable with another separately from joint parts connected to the other ends of the links in the parallel link mechanism.

6. The fine work assistance system according to claim 5, further comprising a sheet-type cover provided over the slave unit except for the predetermined range part replaceable with another separately from the joint parts of the end effector,
wherein the predetermined range part of the end effector is detachably attached to the joint parts even if the cover is provided.

7. The fine work assistance system according to claim 1, wherein the input mechanism of the operation input unit has a hydraulic cylinder mechanism in which a volume of a hydraulic fluid room in a cylinder changes according to a movement of an internal piston reciprocating in response to a user operation, and the hydraulic cylinder mechanism includes a rolling diaphragm that divides an interior of the cylinder into an area of the internal piston and the hydraulic fluid room while being deformed according to the movement of the internal piston, the rolling diaphragm keeping a fluid-tight state between the internal piston and the hydraulic fluid room.

8. The fine work assistance system according to claim 1, wherein the support mechanism unit of the master unit includes a braking unit capable of generating a braking force as a reaction force against an operating force for moving the operation input unit by the user, and when the end effector of the slave unit moved in response to the user operation on the operation input unit reaches a movable limit position, the braking unit is activated to apply a predetermined braking force in response to a user operation for further moving the operation input unit of the master unit to an area outside the movable limit of the slave unit.

\* \* \* \* \*

UNITED STATES PATENT AND TRADEMARK OFFICE
CERTIFICATE OF CORRECTION

| | |
|---|---|
| PATENT NO. | : 11,110,594 B2 |
| APPLICATION NO. | : 15/773858 |
| DATED | : September 7, 2021 |
| INVENTOR(S) | : Susumu Oguri, Makoto Hashuzume and Masaharu Murata |

It is certified that error appears in the above-identified patent and that said Letters Patent is hereby corrected as shown below:

On the Title Page

Item (73) Assignee should read --F. MED Co., Ltd., Fukuoka (JP)--

Signed and Sealed this
Eighteenth Day of October, 2022

*Katherine Kelly Vidal*

Katherine Kelly Vidal
*Director of the United States Patent and Trademark Office*